United States Patent [19]
Hirshowitz et al.

[11] Patent Number: 5,893,879
[45] Date of Patent: *Apr. 13, 1999

[54] APPARATUS FOR THE CLOSURE OF WIDE SKIN DEFECTS BY STRETCHING OF SKIN

[75] Inventors: Bernard Hirshowitz; Amnon Levy, both of Haifa; Alexander R. Gilat, deceased, late of Haifa, by Eitan Rogel, as legal representative; Eitan Rogel, Haifa, all of Israel; Jeffrey Stein, Milford, Conn.; Julian Borgia, deceased, late of Belle Mead, by Lee Ann Borgia, as legal representative; Charles L. Putnam, Bellemeade, both of N.J.; Paul DiCesare, Norwalk; Daniel Rodak, Milford, both of Conn.; Thomas Whitlock, Bridgewater, N.J.

[73] Assignee: MedChem Products, Inc., Princeton, N.J., NJ

[*] Notice: This patent is subject to a terminal disclaimer.

[21] Appl. No.: 08/367,136
[22] PCT Filed: May 3, 1993
[86] PCT No.: PCT/US94/05029
  § 371 Date: Jul. 12, 1995
  § 102(e) Date: Jul. 12, 1995
[87] PCT Pub. No.: WO94/26173
  PCT Pub. Date: Nov. 24, 1994

Related U.S. Application Data

[63] Continuation-in-part of application No. 08/055,413, May 3, 1993, Pat. No. 5,486,196, which is a continuation-in-part of application No. 07/835,636, Feb. 13, 1992, Pat. No. 5,263,971, and application No. 29/003,751, Dec. 3, 1992, Pat. No. Des. 352,356.

[51] Int. Cl.$^6$ ............................................. A61B 17/04
[52] U.S. Cl. ........................ 606/218; 606/213; 606/216; 606/217
[58] Field of Search .................... 606/212, 213, 606/215–218, 150, 148, 151, 149, 201

[56] References Cited

U.S. PATENT DOCUMENTS

| | | | |
|---|---|---|---|
| 376,441 | 1/1888 | Hughes | 606/218 |
| 4,506,669 | 3/1985 | Blake, III | 606/218 |
| 4,535,772 | 8/1985 | Sheehan | 606/218 |
| 5,127,412 | 7/1992 | Cosmetto et al. | 606/232 |
| 5,236,973 | 8/1993 | Cook | 606/216 |
| 5,507,775 | 4/1996 | Ger et al. | 606/218 |

FOREIGN PATENT DOCUMENTS

| | | | |
|---|---|---|---|
| 1412751 | 7/1988 | U.S.S.R. | 606/216 |
| 1556666 | 4/1990 | U.S.S.R. | 606/218 |

*Primary Examiner*—Gary Jackson
*Attorney, Agent, or Firm*—Fulbright & Jaworski LLP

[57] ABSTRACT

An apparatus for closing wide skin defects may be used with two long interdermal needles configured for insertion underneath skin close to margins of a skin defect. The skin closing apparatus may include two retaining members (70, 71) configured as a flange connecting two legs (20) and forming a U-shaped profile. Each of the legs may include either a sharp book (23) or a blunt skin insertion element at the end of the leg adapted for percing the skin and engaging one of the long interdermal needles. Alternatively, the retaining members may include topical engagement elements for engaging portions of the interdermal needles which are located above the skin surface. A contracting mechanism such as a screw (82) may connect the retaining members and approximate the interdermal needles, while bringing the skin margins together until final closure of the skin defect results. One of the retaining members may be fixed to the screw shaft while the other may be releasably connected to the screw shaft by an intergral locking mechanism (85). The skin closing apparatus may also include a clutch mechanism (110) configured to disengage the screw from a knob (81) or handle, when a predetermined force is met or exceeded. Each retaining member of the skin stretching device may include a base segment connected to a pivotal needle carrier by a flexible pivot segment (132). Each retaining member may also include a base segment, which carries the skin insertion needles, removably connected to the body of the skin stretching device. Each base segment may further include a male and/or female connector (143, 144) for engaging a connector (146, 148) on an opposing base member. The retaining members of the skin stretching device may also include skin insertion needles which may be adjustably positioned. The apparatus may further include a device for shielding (176) the sharp points of the skin insertion needles.

99 Claims, 23 Drawing Sheets

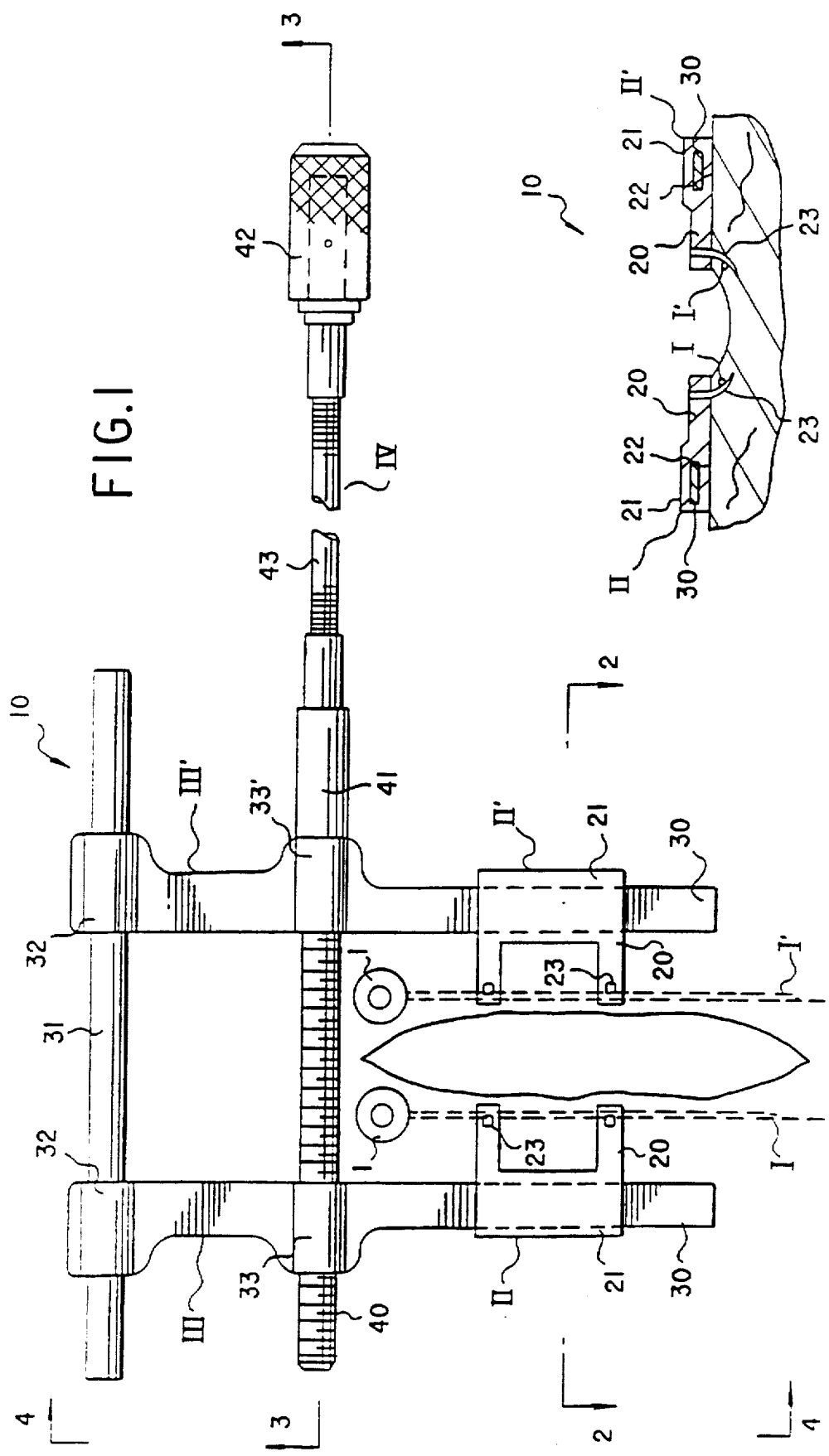

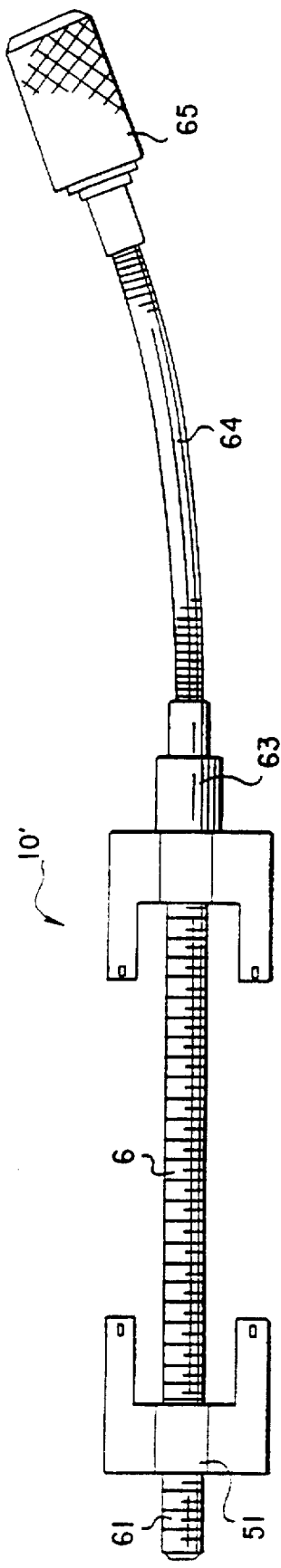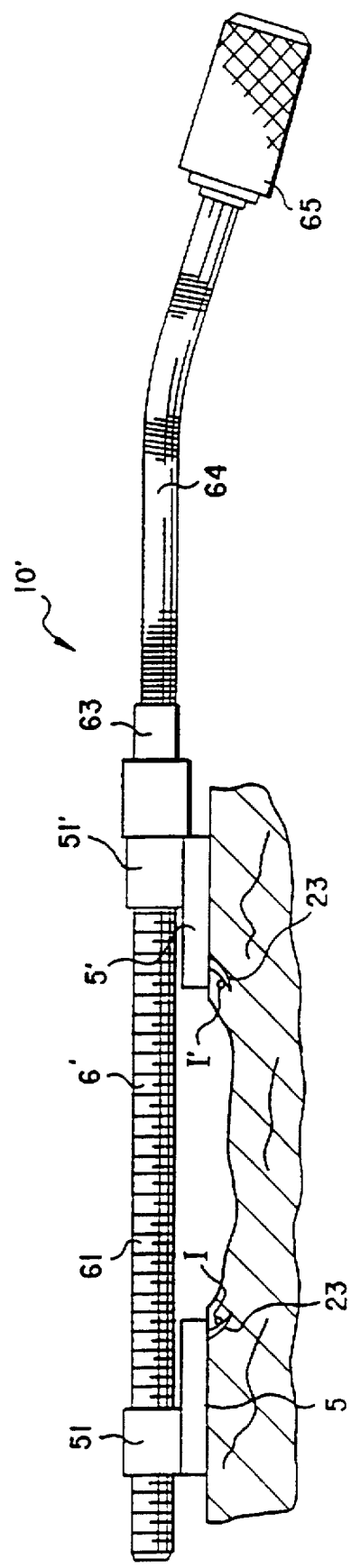

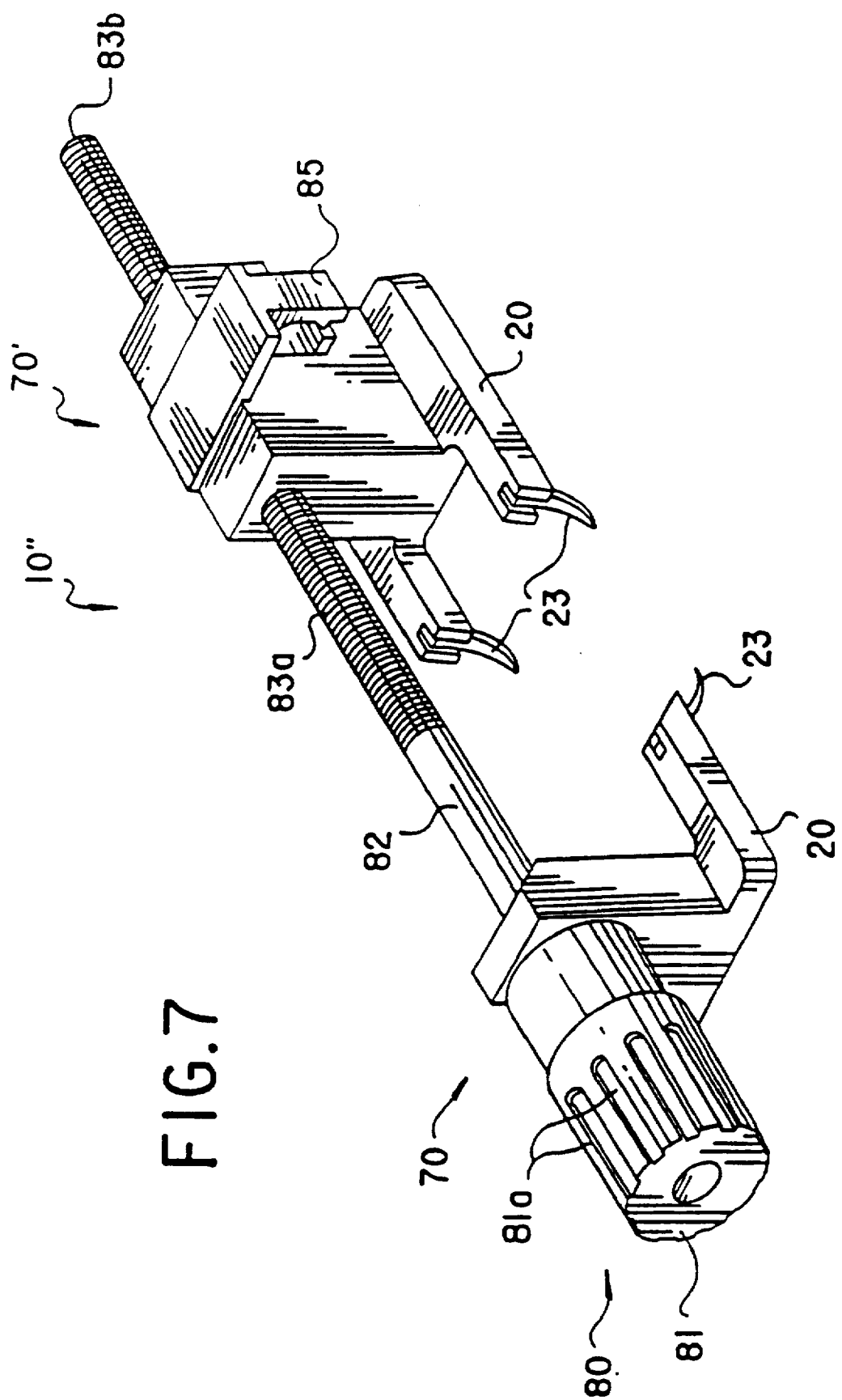

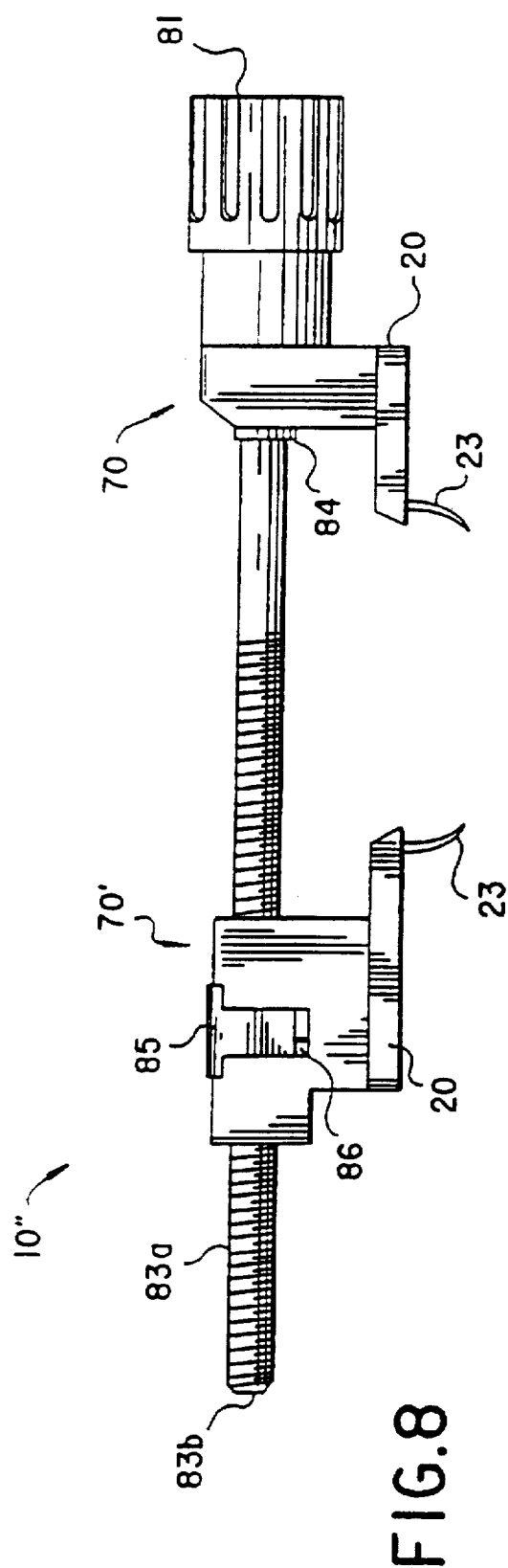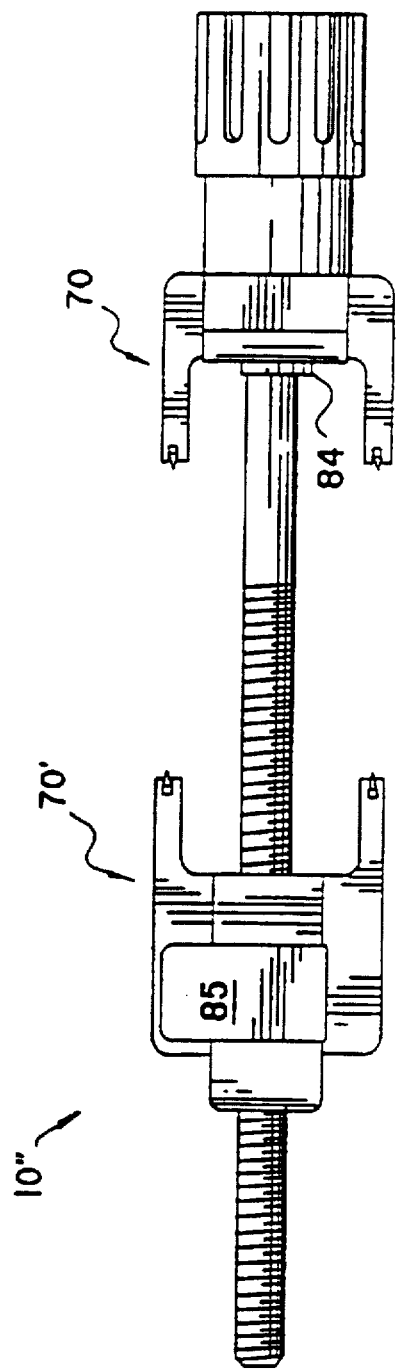
FIG.8
FIG.9

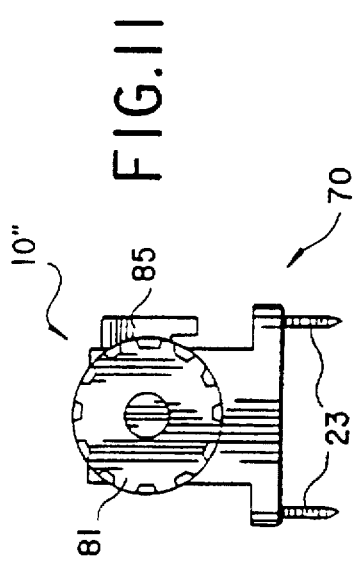
FIG. 11
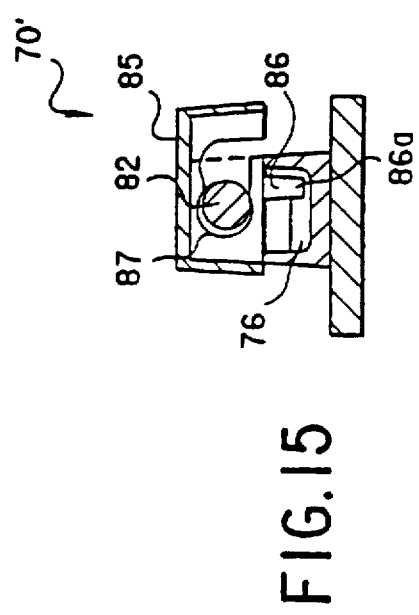
FIG. 14
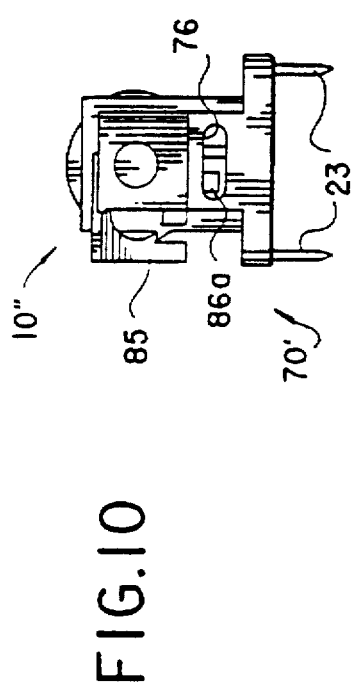
FIG. 10
FIG. 15

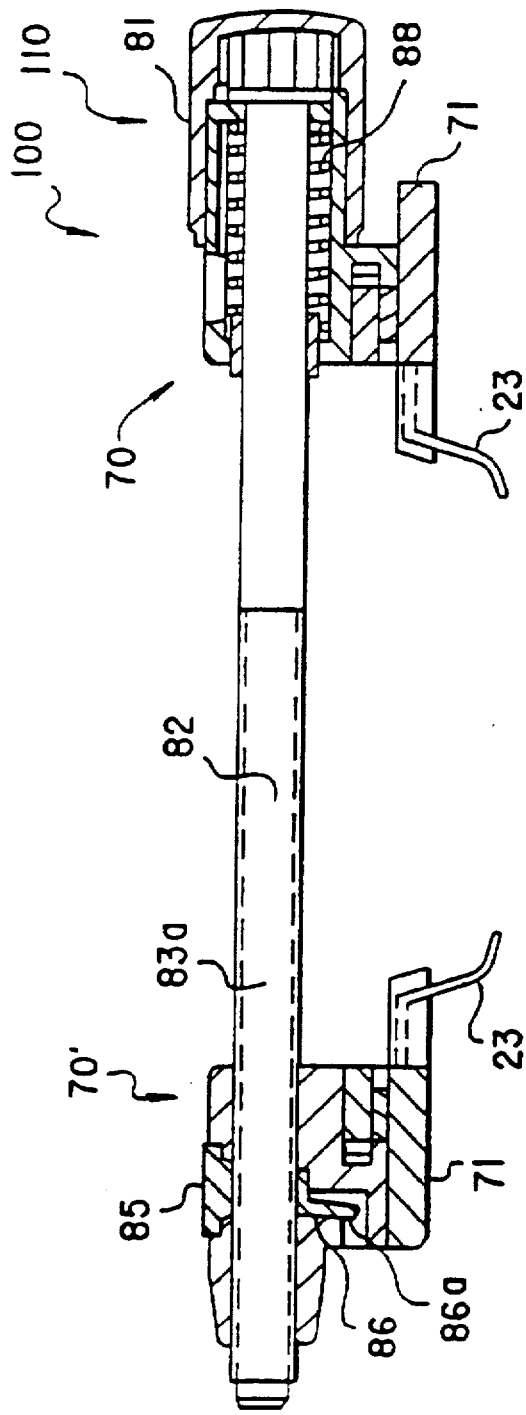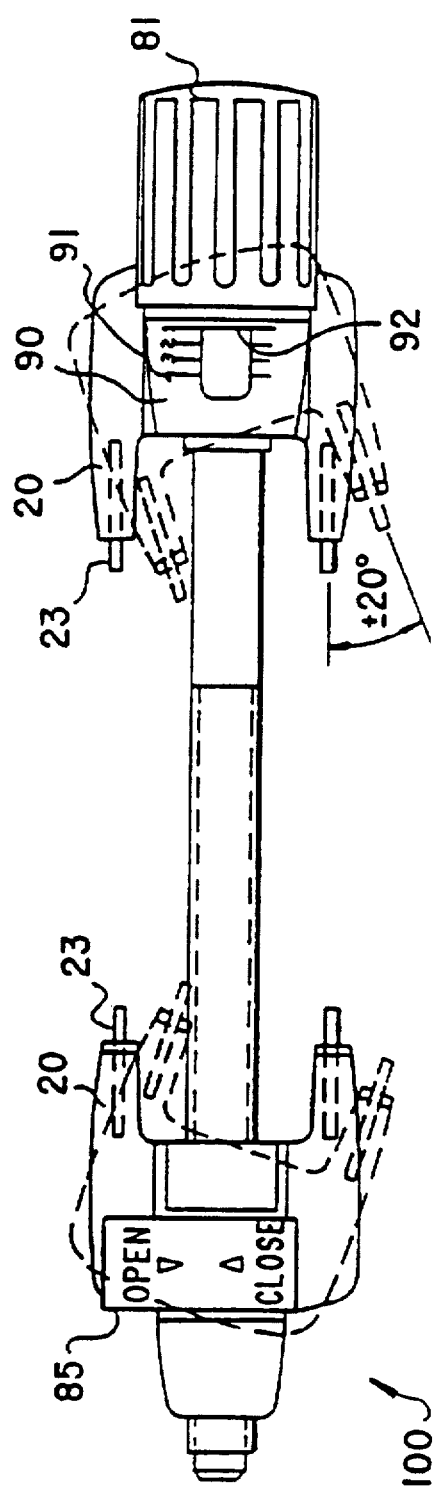

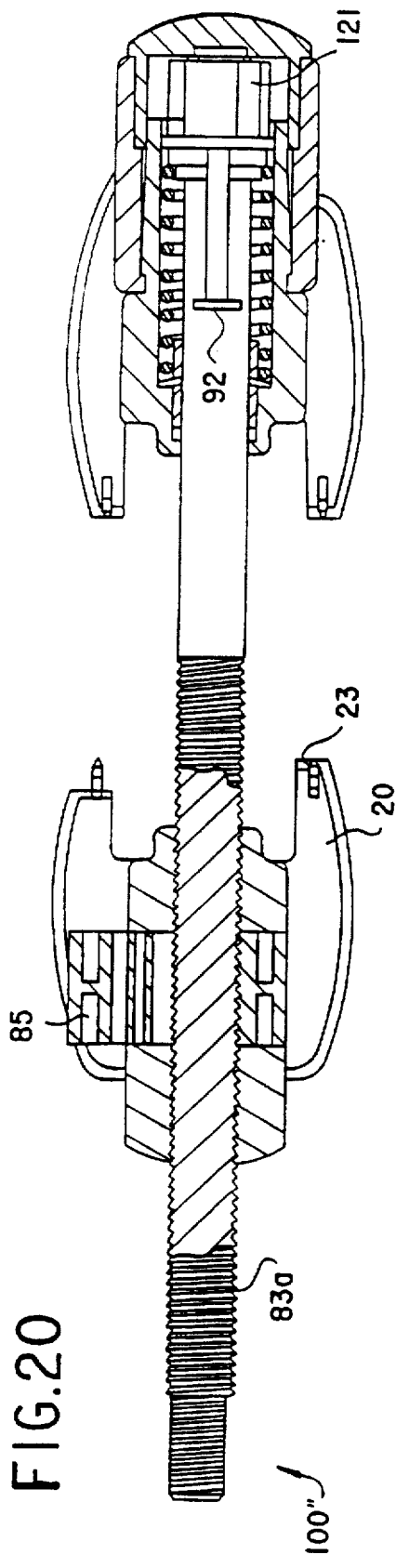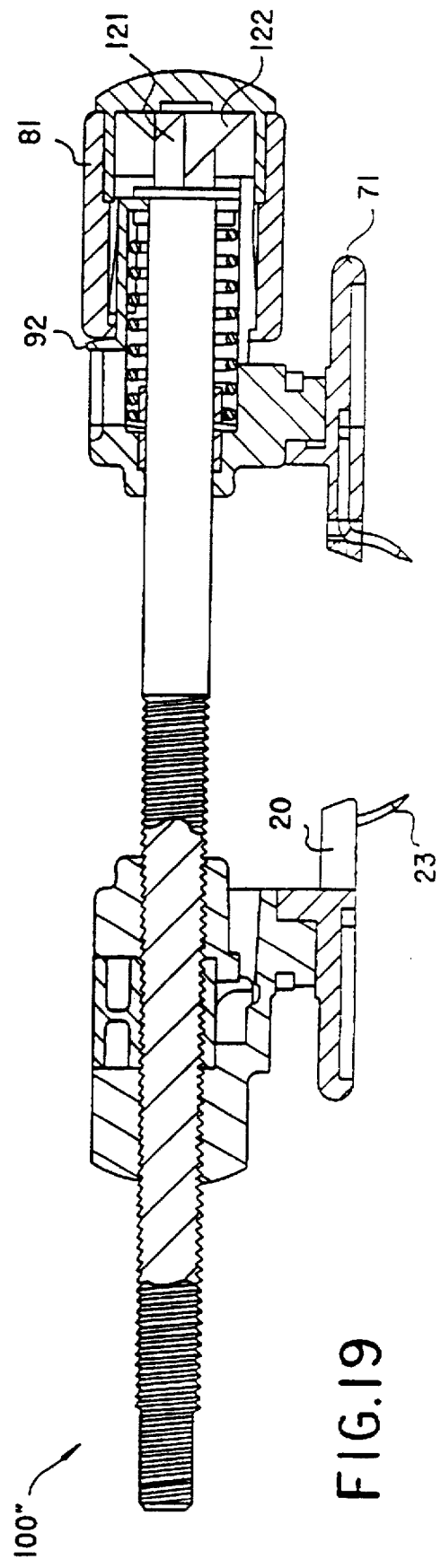
FIG.20
FIG.19

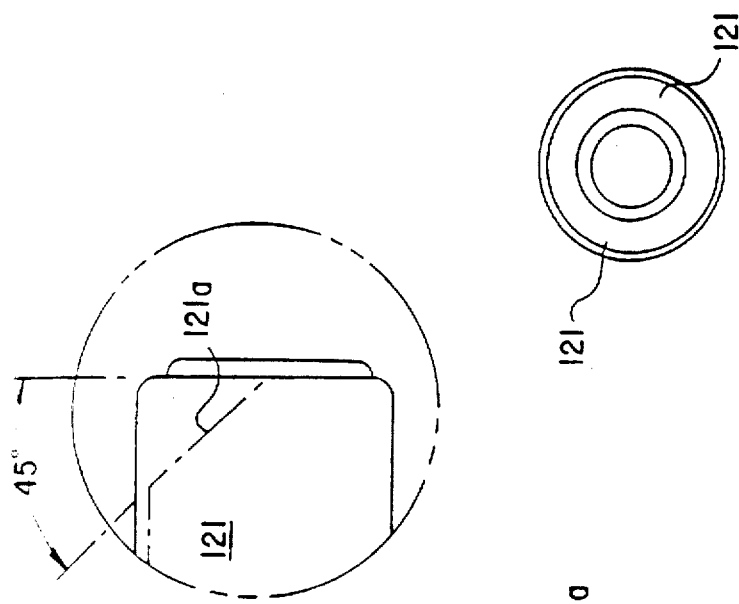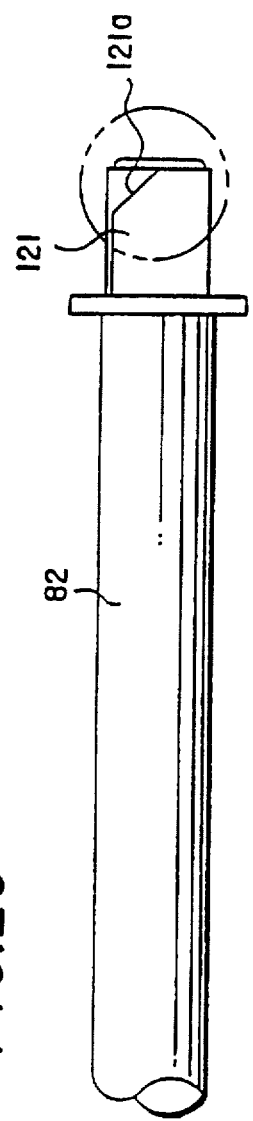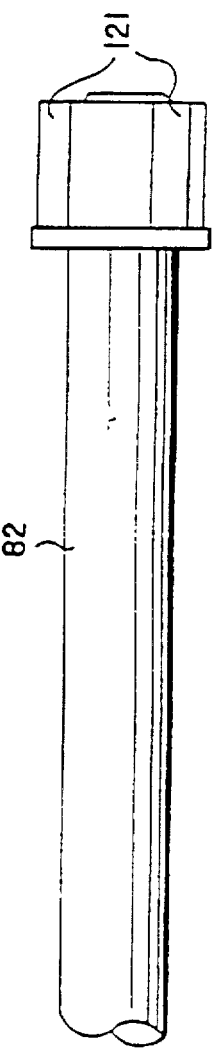

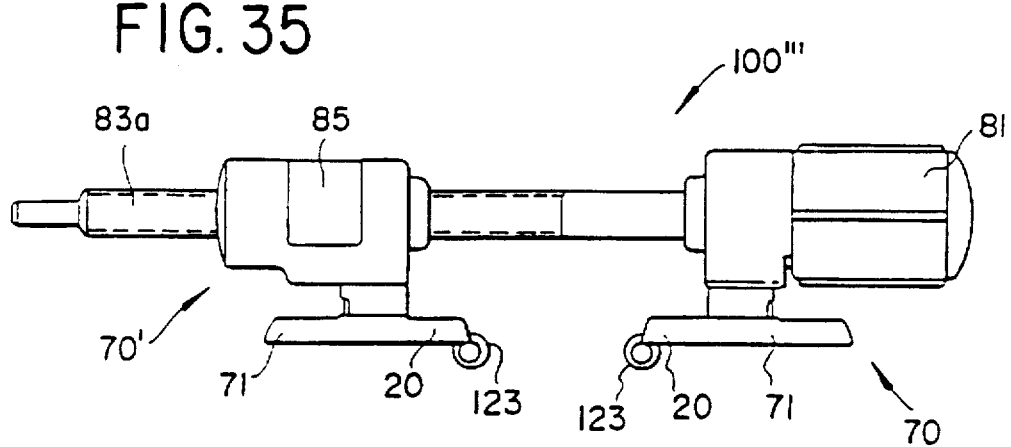
FIG. 35
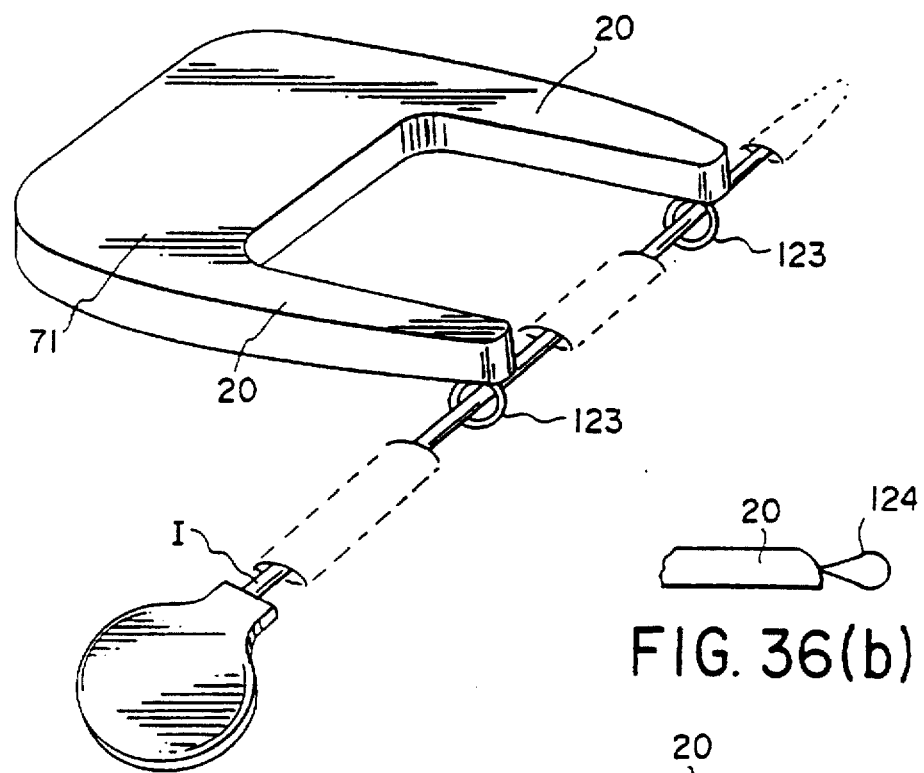
FIG. 36(a)
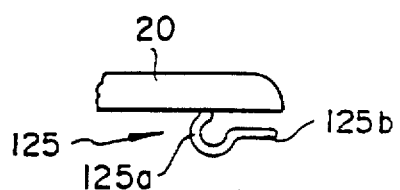
FIG. 36(b)
FIG. 36(c)
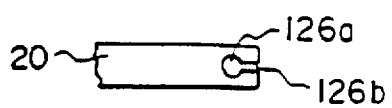
FIG. 36(d)

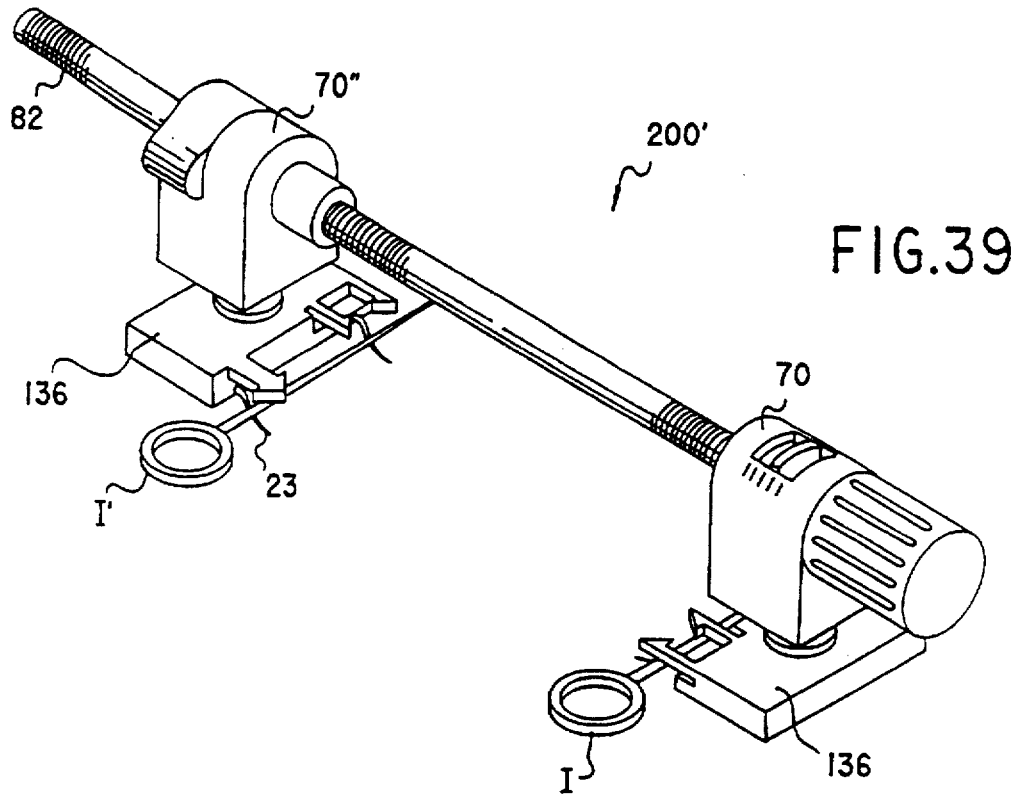
FIG.39
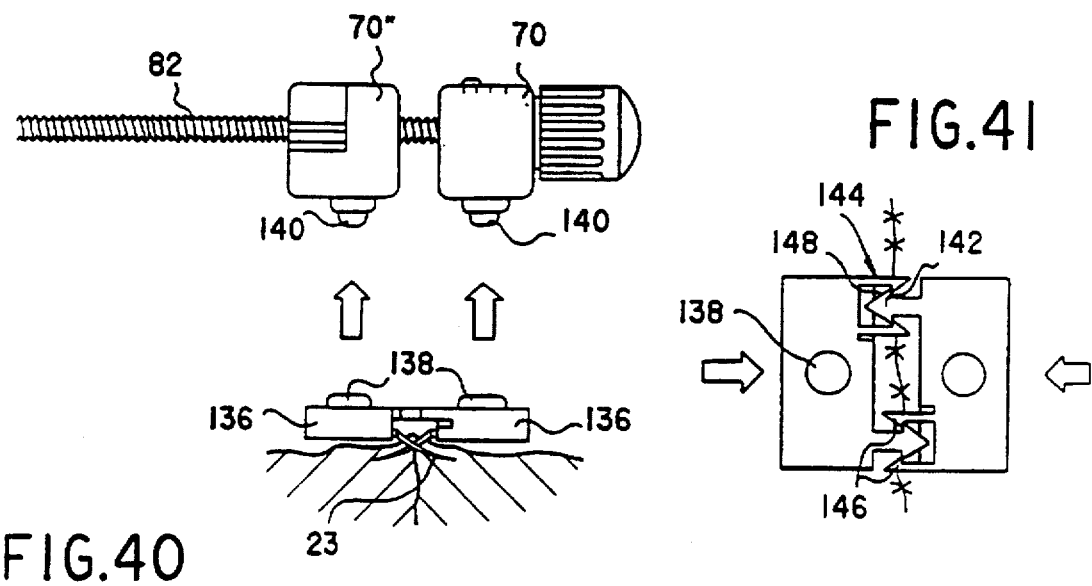
FIG.41
FIG.40
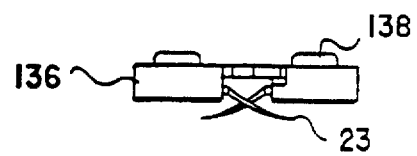
FIG.42

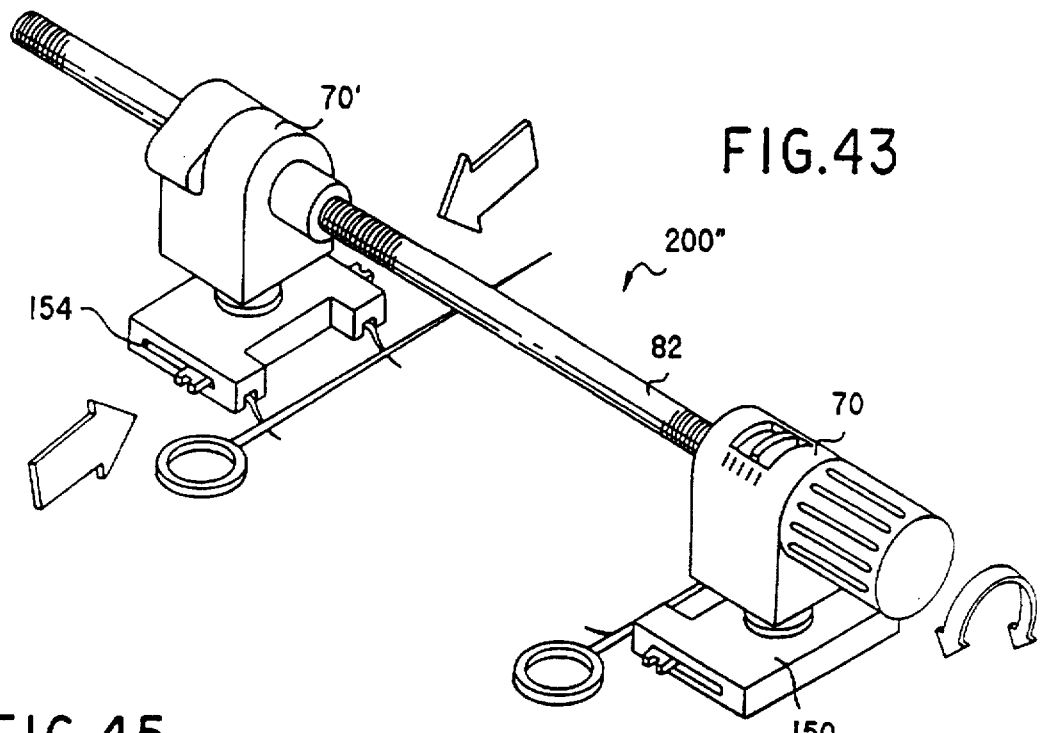
FIG. 43
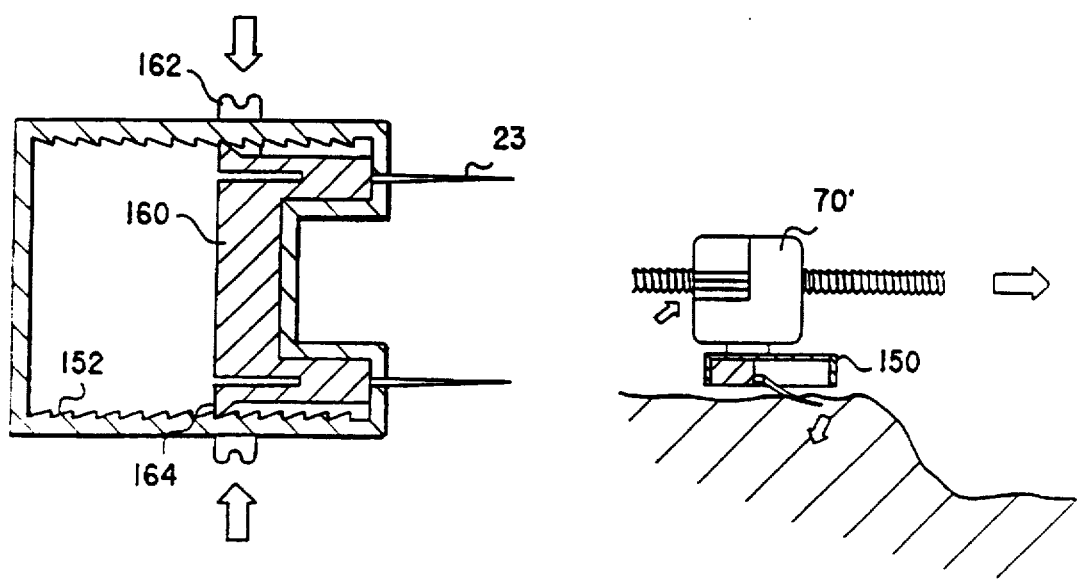
FIG. 45
FIG. 44
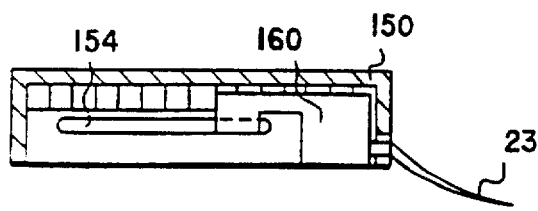
FIG. 46

FIG.50
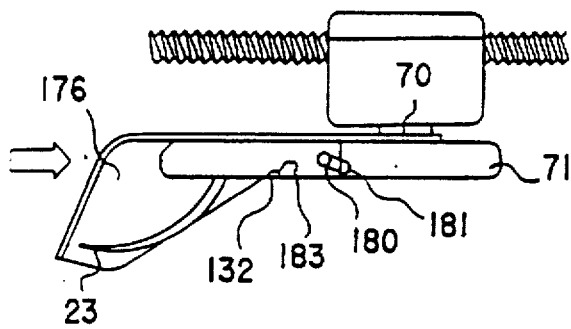
FIG.52
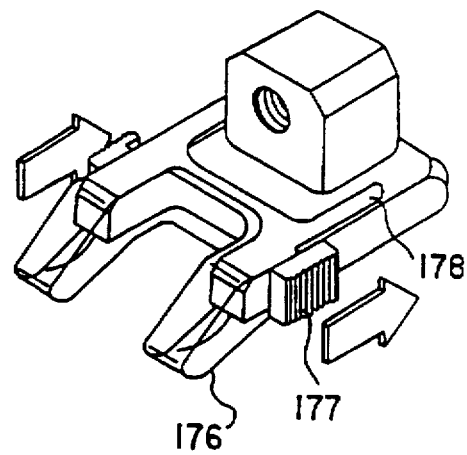
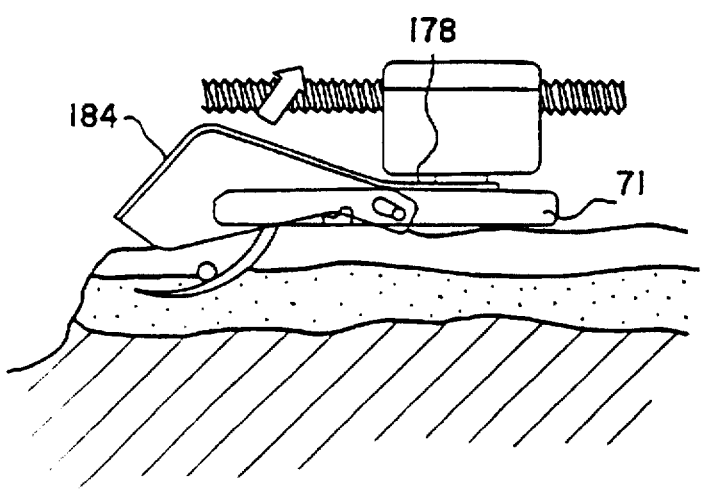
FIG.51

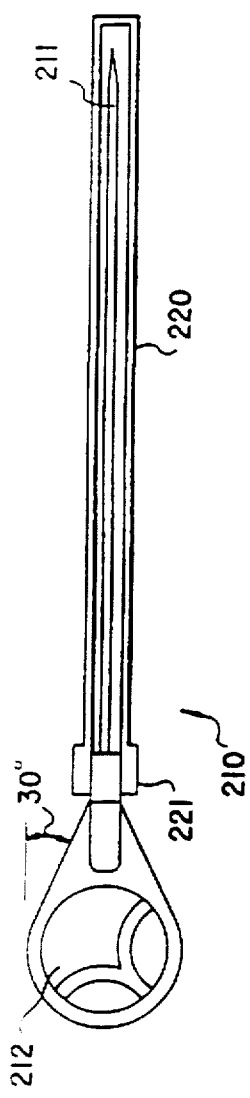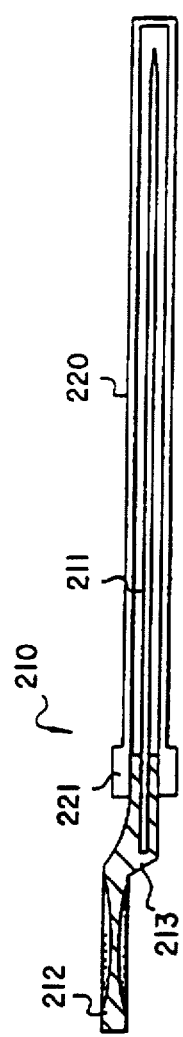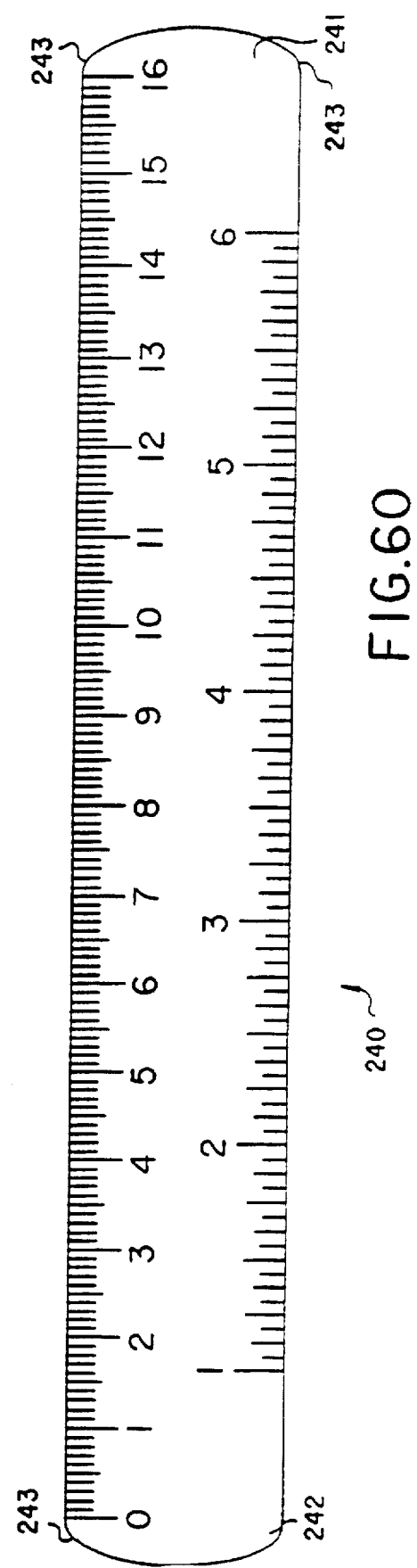

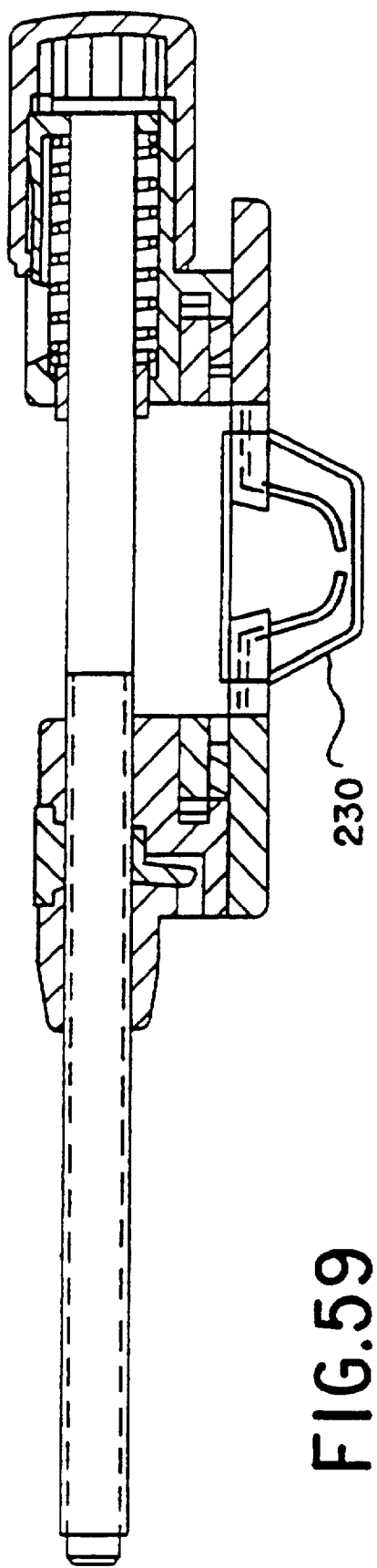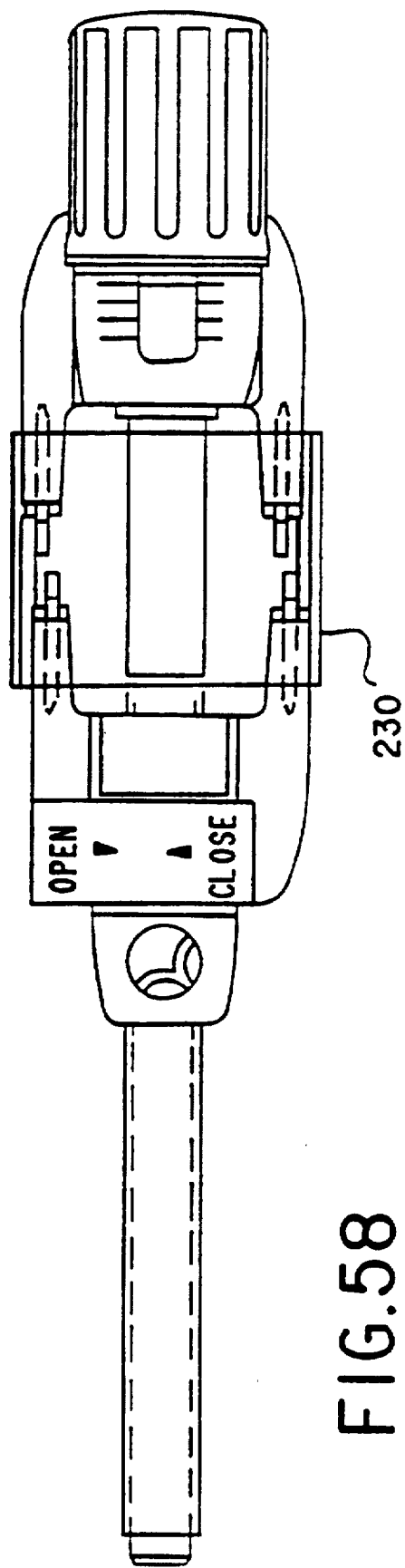
FIG.59
FIG.58

APPARATUS FOR THE CLOSURE OF WIDE SKIN DEFECTS BY STRETCHING OF SKIN

CROSS-REFERENCE TO RELATED APPLICATIONS

This is a continuation-in-part of U.S. patent application Ser. No. 08/055,413 filed May 3, 1993, U.S. Pat. No. 5,486,196 now; which is a continuation-in-part of U.S. patent application Ser. No. 07/835,636, filed Feb. 13, 1992, now U.S. Pat. No. 5,263,971 and U.S. Design patent application Ser. No. 29/003,751, filed Dec. 3, 1992, now U.S. Design Pat. No. 352,356.

BACKGROUND OF THE INVENTION

1. Field of the Invention

The invention relates to an apparatus for stretching skin to cover an open wound, and more particularly, to an apparatus for use before or during an operation for closure of skin defects or otherwise damaged skin areas.

2. Description of the Related Technology

U.S. Pat. No. 4,896,680 discloses a method and apparatus for stretching skin over a wound by load cycling. A force may be applied on opposite skin margins during several periods interrupted by relaxation periods, so skin may be stretched over a wide area. A surgical stretching apparatus according to that patent may include two pins for insertion into the skin along both edges of a wound.

The pins may be gradually pulled together by a flexible strap. The tension or pulling load on the pins may be applied in intervals to allow the collagen fibers of the skin to rearrange for further stretching. The pins may be substantially shaped as safety pins exhibiting a loop for attachment to a flexible strap. The strap may exhibit projections or apertures for engaging a ratchet-shaped device that may hold the pins in forceful apposition.

A disadvantage of the above-described apparatus is manifest when the pins have been drawn together, as no space or room is provided for suturing the approximated skin margins. Another drawback resides in the rather crude manner for approximating the pins, i.e., manually pulling on the flexible strap, as the pulling force cannot be minutely controlled. Another drawback is the two pins grip only relatively narrow strips of skin along both edges, therefore, it is not possible to close a wide wound in a single pulling operation.

There exists a need for a skin closing or skin stretching device that closes a wide skin defect in a single pulling operation. There further exists a need for a skin closing apparatus that provides a visual or auditory indication of the tension or force applied to the wound margins during a pulling operation, and may limit the amount of force applied to the wound margins by disengaging a clutch mechanism.

SUMMARY OF THE INVENTION

The present invention is directed to a skin stretching apparatus that approximates opposing margins of a wound in a single skin stretching operation, provides visual or auditory indication of the amount of force applied and limits the amount of force applied to the margins of the wound. A skin stretching apparatus having the features of the present invention may include two long interdermal needles for insertion under skin along the two edges of a wound to be closed; two retaining members exhibiting a top surface, a bottom surface configured for placement close to the skin, and a sharp hook at the end of each leg of the lower surface of the retaining member. A contracting mechanism may also be provided for pulling and approximating the two retaining members with their legs extending towards an open wound. The skin stretching apparatus may further include a clutch mechanism for preventing overtensioning of the device and a visual or auditory mechanism for indicating the force applied to the wound margins and also for indicating skin relaxation.

The retaining members may be placed behind the interdermal needles with respect to the wound location and in opposing alignment. The hooks of the retaining members may pierce the skin and engage an associated long interdermal needle in a position along the wound edges. The contracting mechanism may be designed to pull the retaining members slowly and gradually together so no damage to the skin area results. Each retaining member may exhibit a U-shaped profile which permits suturing of the skin edges, while the apparatus remains in position proximal to the wound due to the open spaces left between and on both sides of the two legs.

One embodiment of the contracting mechanism exhibits two contractor arms in parallel alignment and connected by a screw mechanism adapted to slowly bring together or approximate the two components by rotating the screw mechanism. One end of each contractor arm may be configured in the shape of a bar having a smooth, even cross-section adapted to carry a retaining member, so the retaining members are maintained in substantially opposite alignment along both sides of a wound, while allowing shifting of each retaining member along its respective bar.

The contractor arms may be slidable connected at their other ends by a smooth bar engaging bores in corresponding locations of the contractor arms with the two arms in parallel alignment. Each retaining member exhibits two legs with outwardly bent hooks at a bottom surface of an end of each leg and connected by a longitudinally perforated flange mounted in a sliding fashion on a smooth bar of a contractor arm.

The two long interdermal needles may be inserted into the skin proximal to the wound margins. The skin closing apparatus is placed across the wound so the retaining members are positioned behind the skin margins.

The hooks of the retaining members may be pressed through the skin into engagement with the interdermal needles. The screw mechanism may be rotated to slowly bring together or approximate the contractor arms and attached retaining members. The operation may be continued in intervals as described in the above patent.

A second embodiment of the apparatus also exhibits two U-shaped retaining members having forwardly bent hooks attached to the underside of the legs at their respective ends. According to this embodiment, each of the U-shaped retaining members exhibits a connecting flange attached to each of the legs. A lug defining a bore may protrude from a top surface of the connecting flange. One lug bore may exhibit a screw thread for engaging a rotatable screw that approximates the U-shaped retaining members, while bringing the retaining members and long interdermal needles together.

A preferred feature of the second embodiment includes a screwthreaded retaining member, a smooth-bored retaining member, and a screw exhibiting a collar at one end for engaging the smooth bore and the screw thread over its remaining length for engaging the screw-threaded retaining member. A drawback of this embodiment, when compared to the first embodiment, is an obstruction caused by the screw location that may hinder or prevent suturing of the wound area between the two legs.

In other embodiments, the skin insertion elements may be replaced by loops, clips, or sutures, or the terminal portion of the leg may itself be configured as an orifice or recess, so that engagement of the long interdermal needle by the skin closing apparatus may be topical. According to this embodiment, the long interdermal needles may be woven through the skin so portions thereof are visible, thereby allowing topical engagement with one or more of the various topical engagement members. The advantage of this embodiment over prior art is that, due to the visibility of the long interdermal needles, engagement may be accomplished without repeated stabbing into the skin with the skin insertion elements. Further, due to the nature of the topical engagement elements, engagement may be more secure, reducing the potential for disengagement of the topical engagement member from the long interdermal needles during the skin defect closure process.

In a further embodiment, the skin closing apparatus may be provided with pivotal base elements or needle carriers situated on both the fixed and movable retaining members of the skin closing apparatus. When the opposing wound margins are not parallel to one another, the pivoting needle carrier automatically adjusts to the geometry of the wound.

In another embodiment, the skin closing apparatus may exhibit removable needle carriers situated on the both the parallel contractor arms of the skin closing apparatus. A removable needle carrier may exhibit at least a female connector with flexible locking tabs, which is displaced and subsequently engaged by opposing a male connector on an opposing needle carrier. After the opposing needle carriers are locked together, the parallel contracting arms and threaded tension bar may be removed while still maintaining wound closure, thereby permitting improved access and visibility for suturing skin margins, as well as the ability to suture in the central area of the needle carriers located between the male and female connectors.

According to a further embodiment of the skin closing apparatus, the skin insertion elements are positioned within the needle carrier so that they may be adjustably positioned once the skin insertion element are inserted into the skin. The principal advantage afforded by adjustable skin piercing element positioning is the ability to trap tissue between the skin piercing elements and the needle carrier thereby preventing rotation of the needles out of the skin once significant stretching force is applied. As the wound margins are brought closer together, it becomes necessary to adjust the skin piercing elements to a forward position in order to bring the skin margins tightly together for suturing.

A further embodiment of the skin closing apparatus provides for automatically shielding the skin piercing elements located on either side of the closure mechanism by providing a flexible shield attached to each retaining member. Tissue approximation is accomplished when the needles and the shield are pressed against the skin; this results in the automatic upward displacement of the shield, thereby exposing the needles so they may penetrate the tissue. The shield protects the user from the exposed needles when the device is not in use, and the shield automatically retracts when the device is engaged with the surface of the skin.

Further embodiments of the skin closing apparatus provide manual devices for shielding the exposed needles of a skin closing apparatus. The principal advantage realized as a result of these devices is user protection from exposed needles.

Another embodiment of the skin closing device includes a pivoting lock for engaging and releasing the moveable retaining member from the screw shaft or tension bar. The lock co-axially engages the threaded tension bar passing through its longitudinal axis. The lock permits the threaded tension bar to shift slightly on its axis, resulting in self alignment of the lock.

Other contracting mechanisms may be provided for approximating the two retaining members. It should be further understood that a significant advantage of the invention resides in the shape of the two retaining members, which permits suturing of the wound margins while the apparatus is still in situ and continues to pull the wound margins together.

It is an object of the invention to provide a skin stretching or closing apparatus which permits suturing of skin edges while the stretching apparatus is in situ without disturbing the suturing operation.

It is another object of the invention to permit insertion into the skin edges of long interdermal needles adapted to grip substantially the entire length of the wound or to permit shifting of the stretching mechanism along the wound edges thereby enabling the interdermal needles to be engaged in different locations.

It is a further object of the invention to permit either reusability or disposability of the apparatus and interdermal needles. According to one object of the invention, a device is provided which can be sterilized after use on one patient and subsequently reused on another patient. According to a second, alternative object, a device having limited reusability is provided which can be used multiple times on the same patient. A third, alternative object is to provide a device which may be disposed after one use.

Another object of the invention is to provide a skin stretching device whereby topical engagement elements engage exposed portions of interdermal needles inserted along margins of a wound without the topical engagement element penetrating the surface of the skin.

A further object of the invention is to allow the needle carrier or base member of the skin stretching device to pivot, permitting the device to adjust to situations where the opposing margins of the wound are not parallel to one another.

Another object of the invention is to provide a skin stretching device where a portion of the device may be removed upon full approximation of the margins of the wound to permit greater access and visibility for suturing the wound in the area surrounded by the skin stretching device.

A further object of the invention is to provide devices for protecting users from inadvertent skin punctures associated with the exposed skin insertion elements.

These and other features, aspects, and advantages of the present invention will become better understood with regard to the following description, appended claims, and accompanying drawings.

BRIEF DESCRIPTION OF THE DRAWINGS

FIG. 1 shows a top plan view of a first embodiment of a skin closing apparatus according to the invention positioned over an open skin wound.

FIG. 2 shows a partial section view of the apparatus taken along line 2—2 of FIG. 1.

FIG. 5 shows a top plan view of a second embodiment of a skin closing apparatus according to the invention.

FIG. 6 shows a side view in partial section of the apparatus of FIG. 5.

FIG. 7 shows a perspective view of a third embodiment of a skin closing apparatus according to the invention.

FIG. 8 shows a side view in elevation of the apparatus of FIG. 7.

FIG. 9 shows a top plan view of the apparatus of FIG. 7.

FIG. 10 shows a front end view of the apparatus of FIG. 7.

FIG. 11 shows a rear end view of the apparatus of FIG. 7.

FIG. 12 shows a top plan view of a fourth embodiment of a skin closing apparatus according to the invention.

FIG. 13 shows a section view in elevation of the apparatus of FIG. 12.

FIG. 14 shows a section view in elevation through a clutch of the apparatus of FIG. 12.

FIG. 15 shows a section view in elevation through a retaining member of the apparatus of FIG. 12.

FIG. 19 shows a section view in elevation of a sixth embodiment of a skin closing apparatus according to the invention.

FIG. 20 shows a plan view in section of the apparatus of FIG. 19.

FIG. 24 shows a partial side view in elevation of a screw shaft or tension bar of the apparatus of FIG. 19.

FIG. 25 shows another partial side view in elevation of the screw shaft or tension bar of FIG. 24, which has been rotated 90°.

FIG. 26 shows an enlarged view of an end of the screw shaft or tension bar, as shown in FIG. 25.

FIG. 27 shows an end view of the screw shaft or tension bar of FIG. 25.

FIG. 35 shows a side view in elevation of a seventh embodiment of a skin closing apparatus according to the invention.

FIG. 36(a) shows an enlarged perspective view of a base member of the apparatus of FIG. 35 exhibiting a topical engagement member shown engaging an interdermal needle.

FIG. 36(b) shows an enlarged side view in elevation of the terminal portion of a base member of the apparatus of FIG. 35 exhibiting a topical engagement member according to a second configuration.

FIG. 36(c) shows an enlarged side view in elevation of the terminal portion of a base member of the apparatus of FIG. 35 exhibiting a topical engagement member according to a third configuration.

FIG. 36(d) shows an enlarged side view in elevation of the terminal portion of a base member of the apparatus of FIG. 35 exhibiting a topical engagement member according to a fourth configuration.

FIG. 39 shows a perspective view of a skin closing apparatus according to a ninth embodiment of the invention.

FIG. 40 shows a side view in elevation of the apparatus of FIG. 39, shown with needle carriers locked together and disengaged from retaining members of the apparatus.

FIG. 41 shows an enlarged top plan view of the needle carriers of the apparatus of FIG. 39 in a locked position.

FIG. 42 shows an enlarged side view of the needle carriers of the apparatus of FIG. 39 in a locked position.

FIG. 43 shows a perspective view of a skin closing apparatus according to a tenth embodiment of the invention.

FIG. 44 shows an enlarged side view in elevation of a movable retaining member of the device of FIG. 43.

FIG. 45 shows an enlarged top sectional view of a needle carrier of the apparatus of FIG. 43.

FIG. 46 shows an enlarged side sectional view in elevation of a needle carrier of the apparatus of FIG. 43.

FIG. 50 shows an enlarged side view in elevation of a retaining member of a skin closing apparatus according to the invention exhibiting a manually locking needle shield.

FIG. 51 shows a side view in elevation of the apparatus of FIG. 50 with the manually locking needle shield in the retracted position.

FIG. 52 shows a perspective view of the apparatus of FIG. 50.

FIG. 56 shows a top plan view of another embodiment of a long interdermal needle according to the invention.

FIG. 57 shows a partial section view in elevation of the long interdermal needle of FIG. 56.

FIG. 58 shows a top plan view of an apparatus according to the invention with a protective covering.

FIG. 59 shows a section view in elevation of the apparatus and protective covering of FIG. 58.

FIG. 60 shows a top plan view of a retractor according to the invention.

DETAILED DESCRIPTION OF THE PREFERRED EMBODIMENT

Figure 4:
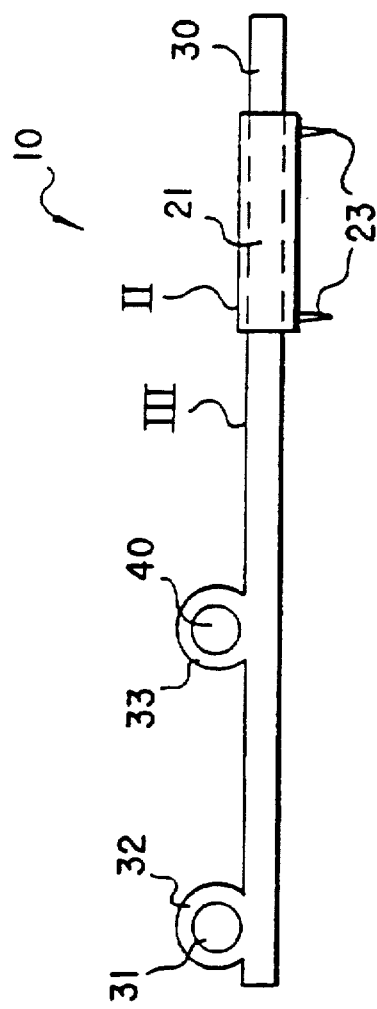
FIG. 4 shows an end view of the apparatus taken along line 4—4 of FIG. 1.
Figure 3:
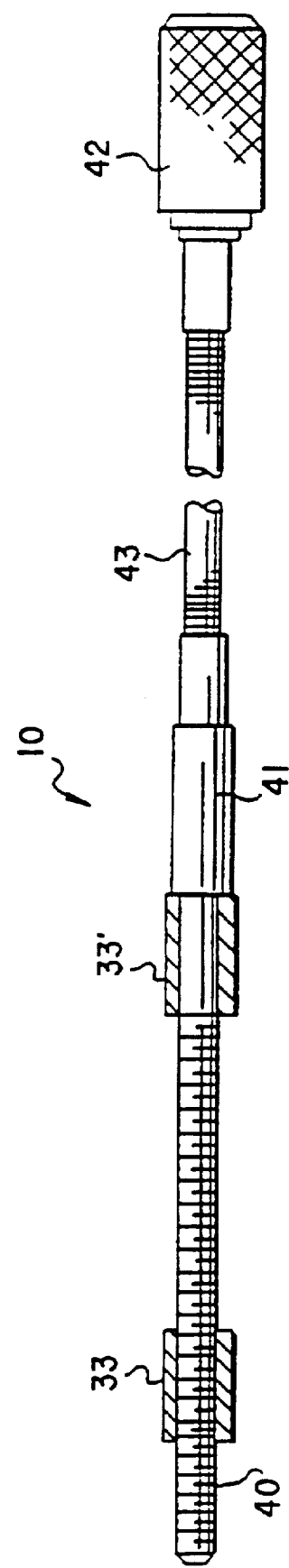
FIG. 3 shows a partial section view of the apparatus taken along line 3—3 of FIG. 1.

FIGS. 1–4 show a skin closing or skin stretching apparatus according to the invention. Skin closing device 10 may be used with two long interdermal needles I, I'. Each interdermal needle may exhibit a head 1 and may be inserted under skin along wound margins as shown in FIGS. 1 and 2. The skin closing device may include two retaining members II, II' for engaging one of the two interdermal needles.

Each retaining member may exhibit a U-shaped profile, and two parallel, spaced-apart legs 20 connected by a flange 21 defining longitudinally directed bore 22 of preferably rectangular cross-section. Each of a plurality of forwardly extending hooks 23 may be connected to an underside of a retaining member. Each of the forwardly extending hooks may be located at an end of a leg 20 of a retaining member.

The hooks, which preferably exhibit a sharp point at the end, may pierce the skin and engage one of interdermal needles I, I' from a side remote from the wound. The retaining members are held in position by two contractor arms III, III' and are slidably mounted on bar-shaped ends 30 along rectangular bores 22. The contractor arms may be held in parallel alignment by a cylindrical bar 31 which extends through horizontal bores in lugs 32 at the other ends of the contractor arms.

A screw IV may pull or bring the contractor arms together and may extend through a screw-threaded bore in a lug 33 on a top surface of arm III and may further extend through a smooth bore in a lug 33' on a top surface of arm III'. Screw IV may exhibit a screw-threaded end 40, a collar 41 abutting lug 33' of contractor arm III' and a handle or knob 42 attached to screw IV by a flexible tube or helical spring 43. By rotating handle 42 the screw-threaded end in engagement with the thread in the lug 33 may pull arms III, III' to each other whereby retaining members II, II' contract the wound margins by hooks 23 and interdermal needles I, I'.

As described in U.S. Pat. No. 4,896,680, a skin closing operation may performed in several stages to allow the skin to stretch in a gradual manner during intervals between the stretching stages. After the skin defect or wound margins have been brought into contact, the wound may be sutured in a manner known to the art, whereby it is evident that legs 20 do not interfere with the operation, as legs 20 are remote from the margins.

FIGS. 5 and 6 show a second embodiment of a skin closing apparatus 10'. Retaining members 5, 5' are approximated or brought together by a screw 6. The retaining members, which are substantially similar to the retaining members of FIGS. 1 and 2, may exhibit perforated lugs 51, 51' on their respective top surfaces. Lug 51 may define a perforation such as screw-threaded bore and lug 51' may define a perforation such as a smooth bore.

Screw 6 exhibits a screw-threaded end 61 cooperating with the screw thread in lug 51 of retaining member 5, a smooth portion (not shown) rotating in lug 51', a collar 63 abutting lug 51' and a flexible operating portion 64 terminating in a knob or handle 65. The skin contracting operation is similar to that described for the above embodiment, however, screw 6 somewhat obstructs the suturing operation.

FIGS. 7–11 show a third embodiment of a skin closing apparatus 10", which exhibits retaining members 70, 70' and a screw 82 for applying skin stretching forces. This embodiment may also be used with two long interdermal needles that are inserted into the skin for distributing closing forces along edges of a wound. A significant advantage provided by the long interdermal needles is the uniform distribution of force across a wide area of skin. Retaining members 70, 70' also exhibit skin insertion elements or hooks 23 connected to each leg 20 for a total of four which engage the long interdermal needles during a skin stretching operation.

Retaining member 70 may be configured as a force supplying retaining member and may exhibit a U-shaped profile. Retaining member 70' may be located opposite a skin defect from retaining member 70 and may also exhibit a U-shaped profile. A contracting mechanism 80 for approximating the retaining members may also be provided.

The contracting mechanism may include a large knob 81 for applying a force and may be located proximal to retaining member 70. The knob may include grooves 81a and/or ridges 81b (see FIG. 17) for facilitating a user's manipulation of the knob. The contracting mechanism may also include a screw shaft or tension bar 82 exhibiting a screw-threaded portion 83a and a distal screw end 83b.

According to the preferred embodiment, the screw shaft exhibits rigidity so bending along the screw axis is minimized. A fiberglass reinforced material may be used, which provides extra rigidity, that is not available from unreinforced material. It is also preferred to use a teflon or silicone filled plastic material. Teflon is preferred as it provides lubrication and keeps the threads running easily and so limits the amount of hysteresis or friction.

Retaining member 70' may also exhibit a reversible lock 85 for releasably locking the retaining member to the screw. The lock 85 exhibits a threaded partial bore for defining a threaded connection and a larger smooth partial bore for allowing the retaining member 70' to slide freely along the tension bar 82. The use may select the engaged position by sliding the lock 85 to engage the threaded partial bore with the screw-threaded portion 83a of the tension bar. The free position is selected by sliding the lock 85 so that the larger smooth partial bore is positioned circumferentially about the screw-threaded portion 83a of the tension bar 82. As best seen in FIG. 10, lock 85 may also include a lock shaft 86 (see FIG. 15) and a lock shaft finger 86a that slides in a slot 76 of retaining member 70'. The reversible lock advantageously allows the user to disengage the retaining members in a quick manner and also to reengage the retaining members in a threaded connection.

The lock exhibits a threaded portion, which allows one to lock the retaining members together. The lock may also be biased i.e., by the resilience of the material selected, so the lock may stay in either the closed or open position.

FIGS. 12–15 show a fourth embodiment of the skin closing apparatus 100, which exhibits retaining members 70, 70' and a screw 82 for applying skin stretching forces. It is also contemplated that two long interdermal needles may be inserted into the skin and may distribute closing forces along edges of a wound, when used with this embodiment. An advantage of the long interdermal needles is the uniform distribution of force across a wide area of skin. Retaining members 70, 70' also exhibit skin insertion elements or hooks 23 connected to each leg 20 for a total of four which engage the long interdermal needles during a skin stretching operation.

This embodiment also exhibits retaining members having swiveling or pivotal base segments 71. As shown in FIG. 12, the preferred amount of pivoting is a rotational motion of about 40°, i.e., about ±20° from a detent mechanism or centering the pivotal base segment about a reference position of the retaining member.

It is also contemplated for the pivotal base segments 71 to pivot throughout a full circular motion of 360°. An advantage realized by providing swiveling or pivotal base segments is that such rotary motion allows the device to conform to irregular force loading, irregular skin motion, or irregular wound margins, thereby avoiding uneven distribution of forces or dislocation of the device. The rotary or pivotal motion of the retaining members allows the device to be compliant with the natural imbalance of the forces encountered in the wound closing.

A force level indictor 90 may also be provided. The force level indicator indicates the force applied along the margins of the skin defect by the contracting mechanism. The force level indicator may include a pointer 92 and a scale using a color scheme or numerals to indicate the varying levels of force applied.

In a preferred embodiment, an objective scale such as numerals 91 represent the different level of force applied to the wound margins. Alternatively, a subjective numerical scale or a color scheme scale, such as green for low level force, yellow for a moderate force application and red for a high force level may be provided.

FIGS. 13 and 14 show a fourth embodiment including a clutch 110 for limiting the forces that may be applied by the contracting mechanism. For the purposes of this application, Applicants define a clutch as any mechanical, electromagnetic or hydraulic or other device for engaging a first rotatable element or shaft to, or disengaging the first element from a second rotatable element or shaft. Accordingly, the clutch may be configured as a frictional clutch or a matching spline system located inside knob 81 and the shaft of the screw.

A compression spring 88 may urge male spline 111 toward female spline 112. According to the preferred embodiment the compression spring is configured so the splines disengage, when a force of about 2.5 kilograms or somewhat higher is applied.

The female spline may be configured as a recess complementing the shape of the male spline and defined by the walls of the knob. As a force or torque is applied to the knob, the indicator which fits through the apparatus and protrudes from the torquing knob, moves forward indicating that larger and larger forces are being applied to the wound margins.

As the skin stretches and those forces decrease, the indicator retracts along the scale and may move along the numerals from 4 to 1. Screw 82 connects the retaining members together so tension is applied to the wound margins as the interdermal needles and retaining members are brought together.

Retaining member 70'may also exhibit releasable lock 85 for providing a threaded connection to the screw. Lock 85 may be configured as a resilient latch which engages the thread and exhibits a resilient structure to remain in either the locked or unlocked position. The resilient nature of lock and lock shaft finger 86a retain the lock within the retaining member. As shown in FIG. 15, finger 86a may be a resilient structure that snaps into engagement with a wall defining slot 76.

This embodiment is preferably sterilized using gamma sterilization. Although conventional sterilization techniques, i.e., ETO sterilization, may also be utilized.

Figure 16:
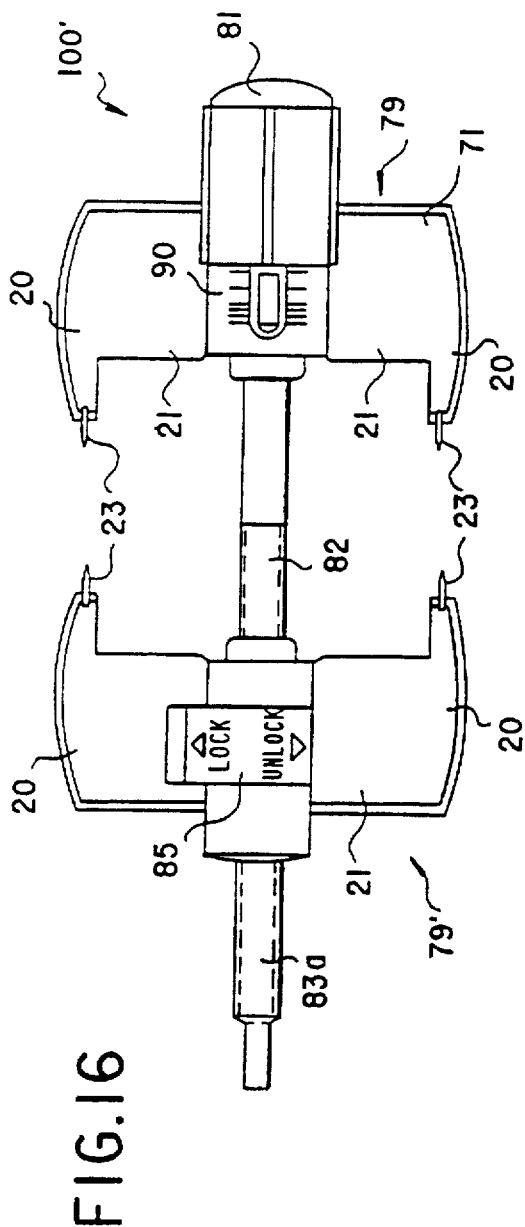
FIG. 16 shows a top plan view of a fifth embodiment of a skin closing apparatus according to the invention.
Figure 17:
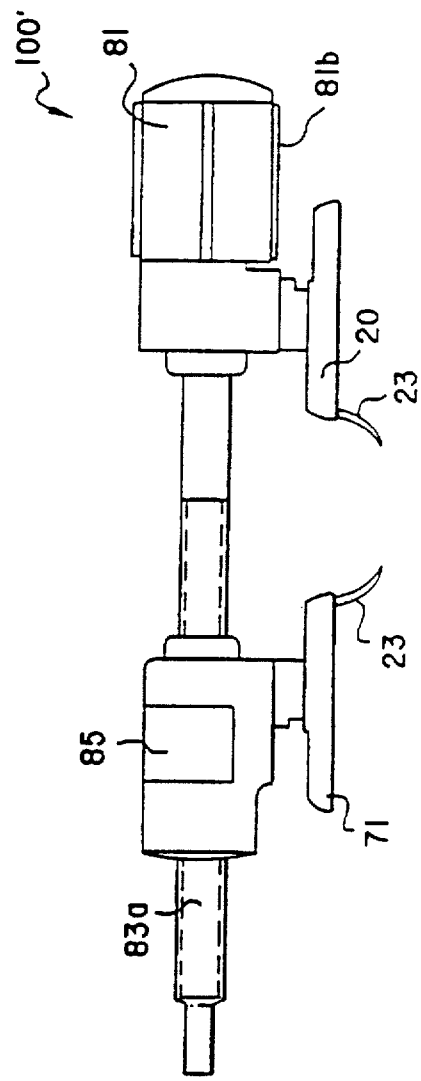
FIG. 17 shows a side view in elevation of the apparatus of FIG. 16.
Figure 18:
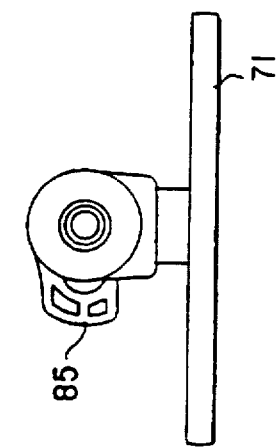
FIG. 18 shows a front end view of the apparatus of FIG. 16.

FIGS. 16-18 show a fifth embodiment of the skin closing apparatus 100', which exhibits retaining members 79, 79' and a screw 82 for applying skin stretching forces. Two long interdermal needles may be inserted into the skin and may transmit closing forces to the skin, when used with this embodiment. Retaining members 79, 79' also exhibit skin insertion elements or hooks 23 connected to each leg 20. According to the preferred embodiment, knob 81 exhibits ridges or protrusions 81b for enhancing tactile sensation, especially when the surgeon is wearing gloves.

This embodiment also exhibits retaining members having swiveling or pivotal base segments 71 with the preferred amount of pivoting is a rotational motion of about 40°, i.e., about ±20° from a central or reference position. This embodiment differs from the previous embodiments as the pivotal base segments are "wide" to eliminate the need for using multiple devices or a single device multiple times to close a skin area.

According to the preferred embodiment shown in FIGS. 12-15, the width of each retaining member is between 20 and 40 millimeters. In the wide embodiment shown if FIGS. 16-18, the greater width of each retaining member (between 40 and 80 millimeters) provides additional stability. Both embodiments are preferably sterilized using gamma sterilization. Although conventional sterilization techniques, i.e., ETO sterilization, may also be utilized.

Figure 21:
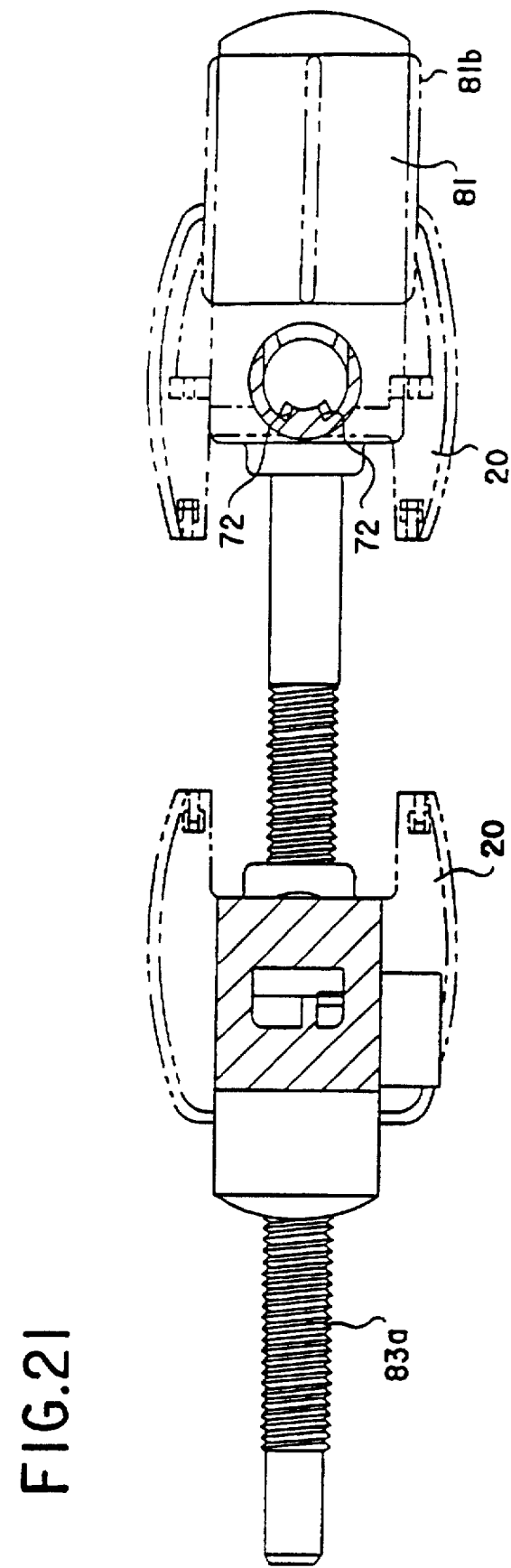
FIG. 21 shows a top plan view in partial section of the apparatus of FIG. 19.
Figure 23:
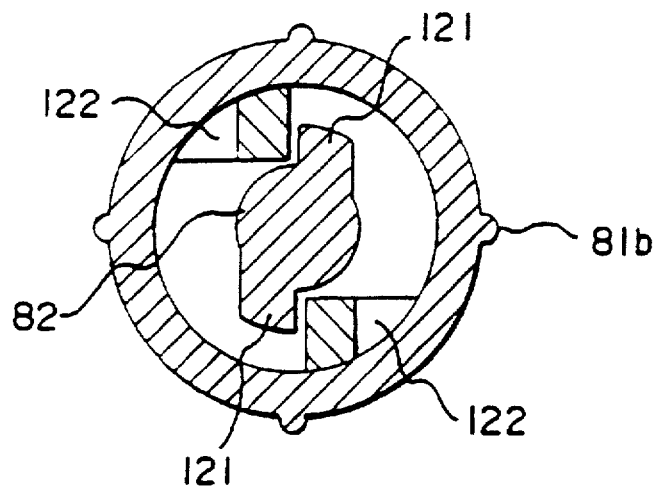
FIG. 23 shows a section view in elevation through a clutch of the apparatus of FIG. 19.
Figure 22:
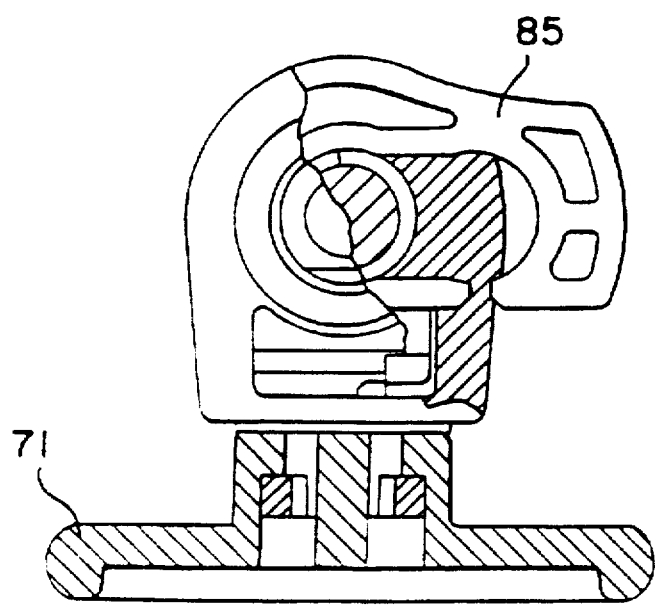
FIG. 22 shows a front view in partial section of the apparatus of FIG. 19.

FIGS. 19-34 show a sixth embodiment of the skin closing apparatus 100", which is substantially similar to the embodiment of FIGS. 12-15. As shown in FIG. 21, the skin closing device according to this embodiment includes stops 72 which limit the rotational movement of the pivotal base segments. This skin closing apparatus according to this embodiment also includes first and second configurations of an improved clutch mechanism. Each configuration of the improved clutch mechanism exhibits two stationary splines 122 that are located in the knob 81 and exhibit inclined contact surfaces 122a.

According to a first configuration of the improved clutch mechanism, as best seen in FIGS. 23-27, one end of the screw shaft 82 exhibits two axially movable splines 121 with oblique contact surfaces 121a, which are preferably inclined at 45° angles. The screw shaft 82 and splines 121 are axially movable in relation to the knob 81. The threaded portion of the screw shaft 82 is omitted in FIGS. 24-27 for purposes of clarity only. The advantage of this clutch element is seen when the splines reengage during skin relaxation. Due to the inclined surfaces, the splines may automatically realign in the initial position. In contrast to this improved clutch, the prior clutch may exhibit misalignment problems if the male and female splines are not centered with respect to each other during realignment. However, problems may arise in the clutch element of this configuration where the splines 121, due to manufacturing tolerances, are non-symmetrically disposed about the rotational axis of the screw shaft 82. When this occurs, the clutch may become jammed when the splines reengage during skin relaxation, due to eccentric dislocation of the shaft resulting in both splines 121 being disposed on the same side of splines 122. Accordingly, very tight manufacturing tolerances must be maintained to ensure that splines 121 are symmetrically disposed about the rotational axis of the screw shaft 82.

Figure 30:
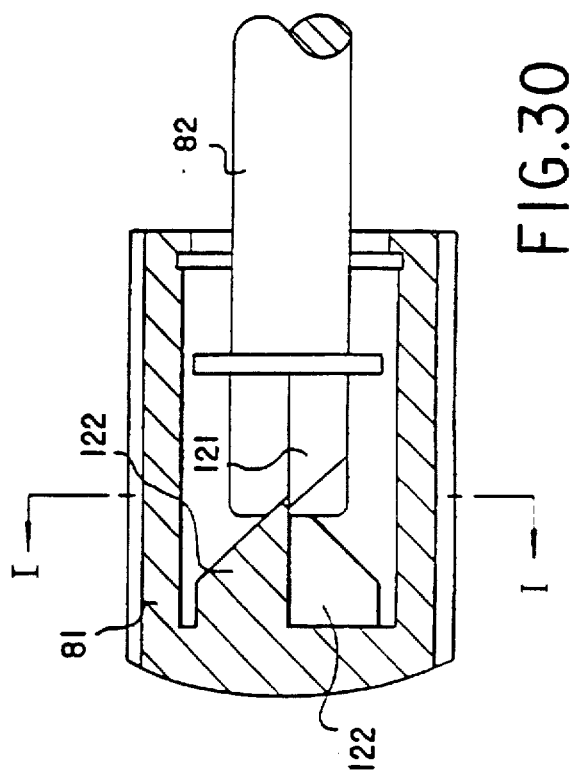
FIG. 30 shows a side section view in elevation of the clutch of the apparatus of FIG. 28.

FIGS. 28-32 show an improved clutch mechanism of the sixth embodiment of this skin stretching apparatus 100"

according to a second configuration, which overcomes the problems inherent in the clutch mechanism according to the first configuration. In this second configuration, the screw shaft 82 exhibits only a single axially movable spline 121 with an oblique contact surface 121*a*. During the axial extension of the screw shaft 82 into the knob, the single spline can always fit between splines 122 of the knob, regardless of its orientation with respect to the splines 122. In contrast to the first configuration, the knob can rotate as required by the shaft, so that the single spline 121 can slip between the splines of the knob. This allows the screw shaft 82 to have eccentricity relative to the knob, as shown in FIG. 30, without the danger of axial binding. As a result, the screw shaft can be axially displaced back into the knob sufficiently for full face engagement of its spline 121 against one of the splines 122 of the knob.

Figure 34:
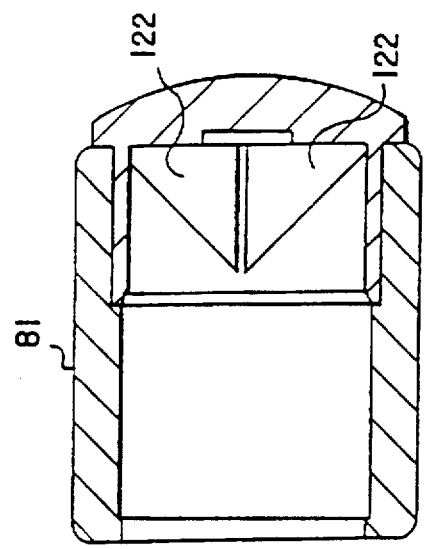
FIG. 34 shows a section view in elevation of the knob of FIG. 33.
Figure 33:
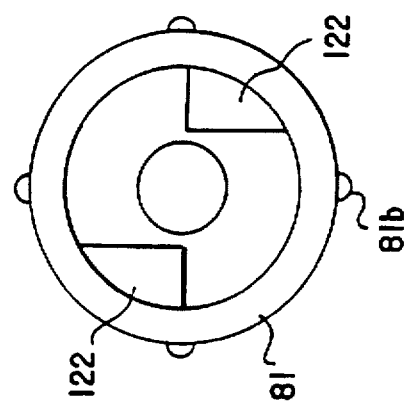
FIG. 33 shows a front view of a knob of the apparatus of FIG. 19.
Figure 28:
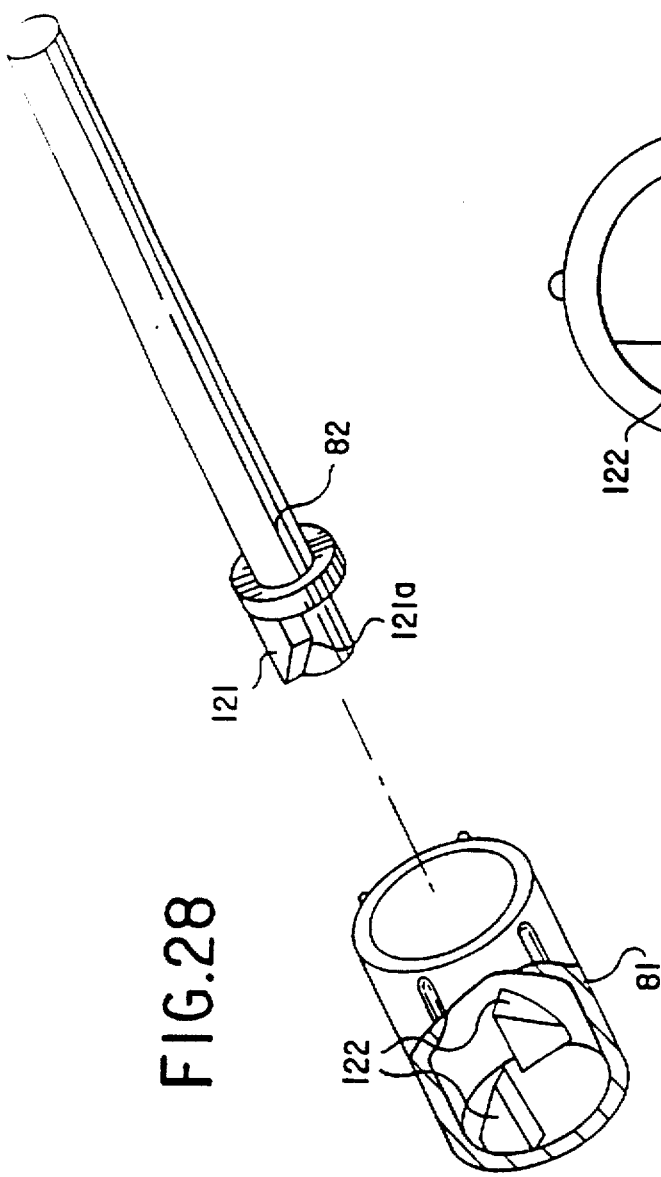
FIG. 28 shows an exploded perspective view of an alternative configuration of a clutch of the apparatus of FIG. 19.
Figure 29:
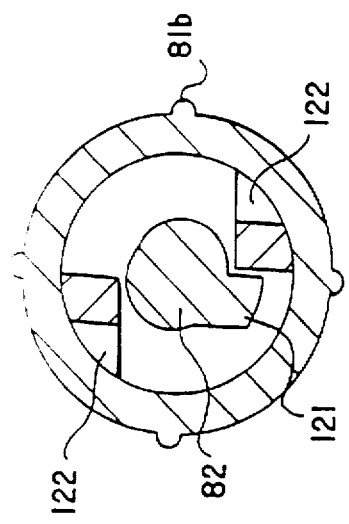
FIG. 29 shows an end section view in elevation through the clutch of the apparatus of FIG. 28.
Figure 32:
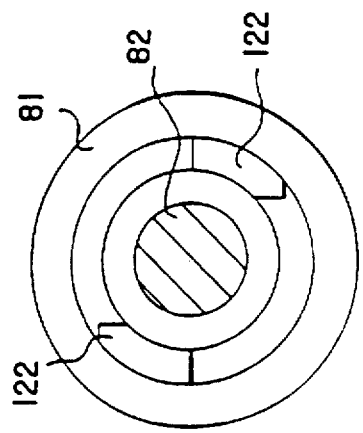
FIG. 32 shows a right end view of the clutch of the apparatus as shown in FIG. 30.
Figure 31:
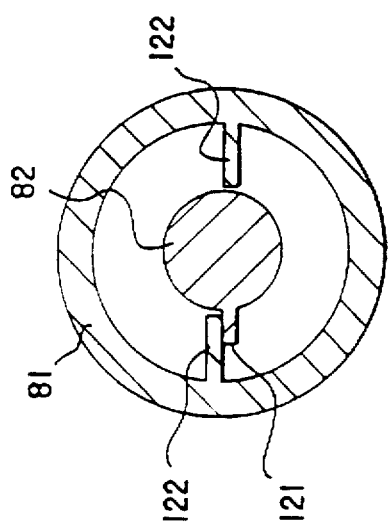
FIG. 31 shows a sectional view of the clutch of the apparatus along the line I—I of FIG. 30.

FIGS. 33 and 34 show enlarged views of the knob with stationary splines 122. The stationary splines 122 exhibit oblique contact surfaces 122*a*, which are preferably inclined at 45° angles.

FIGS. 35–36(*d*) show a seventh embodiment of a skin closing apparatus 100" wherein each retaining member 70, 70' exhibits a base member 71 having a pair of legs 20, each leg further exhibiting a topical engaging member. This embodiment of the skin closing apparatus is similar to previously described embodiments, wherein like reference numerals indicate like components. FIGS. 35 and 36(*a*) show a topical engaging member according to a first configuration in which the terminal portions of the legs 20 may each exhibit a loop 123 connected to the underside or end of the legs 20. The loop 123 may be made from a variety of rigid metallic or plastic materials such as surgical stainless steel, "Lexan" polycarbonate or composite fiber material. As best shown in FIG. 36(*a*), the loops 123 may be engaged topically by exposed portions of long interdermal needles I, I' which are inserted along opposing margins of the skin defect.

FIG. 36(*b*) shows a topical engaging member according to a second configuration in which the terminal portions of each leg 20 may exhibit a suture 124 connected to the underside or end of the leg 20. The suture may be formed from any suitable medically approved filamentary materials. Each suture 124 is preferably configured as a loop. The sutures 124 may be engaged topically by exposed portions of long interdermal needles I, I' which are inserted along opposing margins of the skin defect.

FIG. 36(*c*) shows a topical engaging member according to a third configuration in which the terminal portions of each leg 20 may exhibit a clip 125 connected to the lower surface of the leg 20. The clips 125 may be formed from a variety of semi-rigid metallic, plastic, composite or composite fiber materials. The clips 125 may topically engage exposed portions of the long interdermal needles I, I' which are inserted along opposing margins of the skin defect. Each clip 125 exhibits a curved or recessed portion 125*a* in which the interdermal needle I, I' will securely fit, and a flexible arm portion 125*b*, which allows the skin closing device to be selectively disengaged from the interdermal needles by the user.

FIG. 36(*d*) shows a topical engaging member according to a fourth configuration in which the terminal portions of each leg 20 may exhibit an orifice or recess 126 formed therein to receive one of the long interdermal needles I, I'. The orifices or recesses 126 may topically engage exposed portions of the long interdermal needles I, I' which are inserted along opposing margins of the skin defect. Each recess exhibits a first substantially circular portion 126*a* having a diameter roughly equal to the diameter of an interdermal needle for securely receiving the interdermal needle therein. The recess also includes a second narrow portion 126*b* connected to the first portion of the recess and exhibiting an opening at the terminal portion of the leg 20. The terminal portions of the leg 20 surrounding the narrow portion 126*b* are flexible to allow the skin closing device to be selectively disengaged from the interdermal needles by the user.

Figure 37:
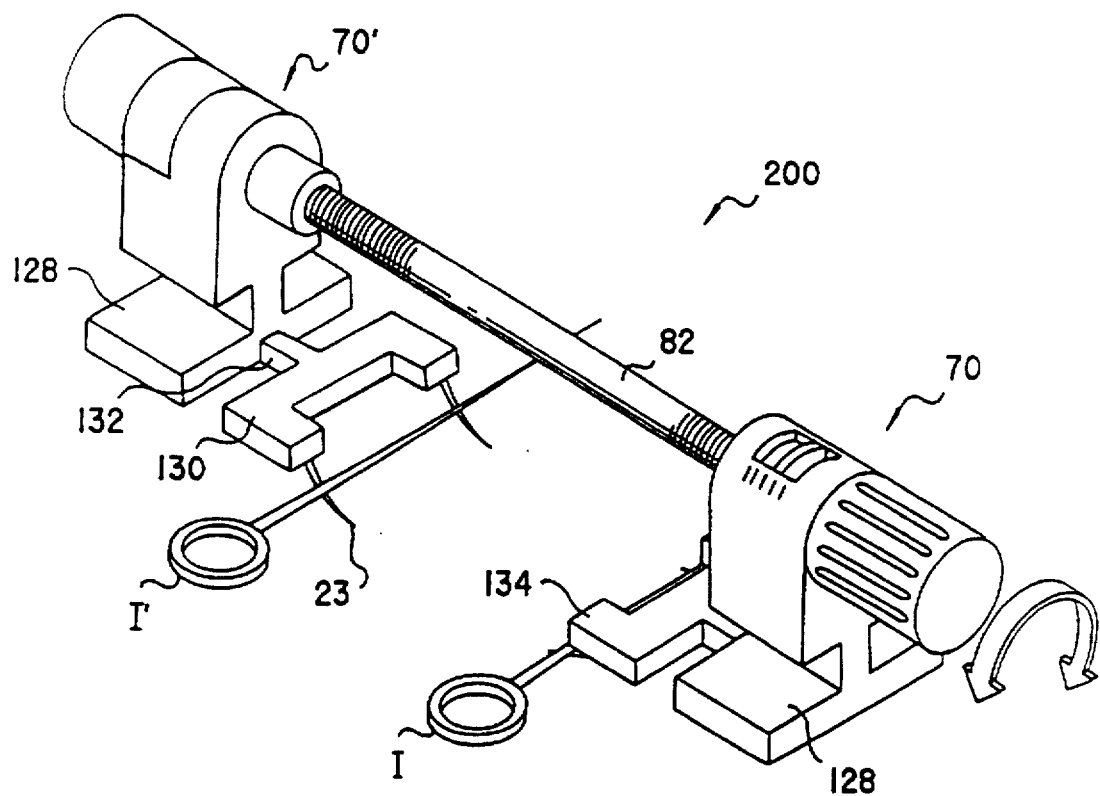
FIG. 37 shows a perspective view of a skin closing apparatus and interdermal needles according to an eighth embodiment of the invention.
Figure 38:
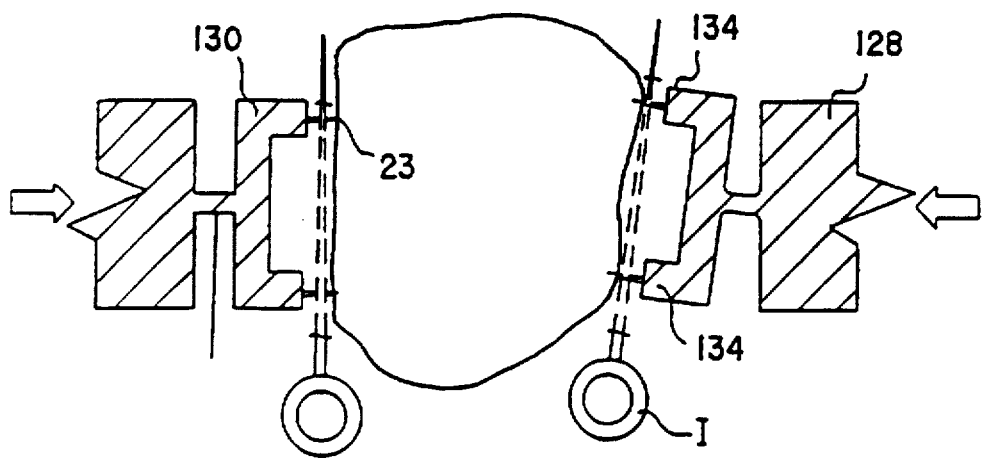
FIG. 38 shows a top sectional view of the needle carriers of the apparatus of FIG. 37 shown engaging interdermal needles along margins of the wound.

FIGS. 37–38 show a further advantageous embodiment of a skin closing apparatus 200 which may exhibit retaining members 70 and 70' and a threaded screw shaft 82 for applying skin stretching forces. Each retaining member may further exhibit a base segment 128 which may exhibit at least one pivotal needle carrier 130. According to this embodiment of the invention, a needle carrier 130 may be flexibly secured to the base segment of each retaining member by conventional means. Further, each needle carrier may exhibit at least one skin piercing element 23 which may be secured to a portion of the needle carrier by any known means. The skin piercing elements 23 are configured to pierce the skin and engage a plurality of interdermal needles I, I' disposed beneath the skin surface along opposing edges of the wound.

According to the preferred embodiment, a flexible pivot 132 may be provided for flexibly securing a needle carrier to a base segment of each retaining member. The needle carrier 130 and the flexible pivot 132 are formed integrally with the base segment 128. The flexible pivot 132 permits geometric variation of the needle carrier relative to the wound margin. Consequently, when the margins of the skin which define the wound are not parallel, the needle carrier 130 may pivot at the flexible pivot 132 to accommodate the actual geometry of the wound. As the wound margins become substantially parallel, the pivoting needle carrier automatically adjusts to the new geometry. Each needle carrier 130 exhibits a pair of inwardly extending legs 134. Each leg 134 exhibits a skin insertion element 23 connected to and extending from a terminal portion of the leg, so as to provide a reliable means of securely positioning the skin closing apparatus thereby affording optimal wound closure performance.

FIGS. 39–42 show a further advantageous embodiment of a skin closing apparatus 200' which may exhibit retaining members 70 and 70' and a threaded screw shaft 82 for applying skin stretching forces. Each retaining member may further exhibit a pivotal base segment or needle carrier 136 which may be removed from the body of the skin closing apparatus 200'. Each needle carrier 136 exhibits at least a male or female locking member for locking the needle carriers together, as shown in FIG. 41, once the margins of the wound have been fully approximated to permit removal of the skin closing apparatus prior to suturing, while maintaining sound wound closure. Each removable needle carrier may exhibit a plurality of skin piercing elements 23 which may be secured to portions of the needle carrier by any known means. The skin piercing elements 23 are configured to pierce the skin and engage a plurality of interdermal needles I, I' disposed beneath the skin surface along opposing edges of the wound.

According to a preferred embodiment, each needle carrier 136 exhibits an engaging receptacle 138 located on an upper surface of the carrier. An engaging stud 140 located on a lower surface of each retaining member 70, 70' is removably disposed in the engaging receptacle 138, thereby providing a releasable connection between each retaining member and its corresponding needle carrier. Each removable needle carrier 136 may exhibit an integral male connector 142 and an integral female connector 144 positioned along its closure side. As the wound margins are brought together, as shown in FIG. 40, each male connector 142 engages a corresponding resilient female connector 144 on the opposing needle carrier. As best seen in FIG. 41, each female connector exhibits flexible locking tabs 146, which are displaced by the male connector, and which lock into lateral projections 148 of the male connector 142 once the opposing margins of the wound have been fully approximated. Once the opposing needle carriers have been locked together, the main body of the skin stretching device may be removed from the wound area leaving only the locked needle carriers in place, as shown in FIG. 40. This permits improved access and visibility to the area proximal to the skin stretching device for suturing skin margins in that area.

FIGS. 43–46 show a further advantageous embodiment of a skin closing apparatus 200" which may exhibit retaining members 70 and 70' and a threaded screw shaft 82 for applying skin stretching forces. Each retaining member may further exhibit a pivotal base segment or needle carrier 150 which may include at least an integral adjustment rack 152 located on parallel interior surfaces of the carrier, at least one slot 154 located in the lateral sides of each needle carrier as shown in FIG. 43, and a needle shuttle 160 movably positioned within the needle carrier body. Each needle shuttle 160 may exhibit a plurality of skin piercing elements 23 positioned and secured thereto by known means, and at least one integral adjustment button 162 which may be positioned in a coplanar orientation relative to the shuttle body, and which may be integrally associated with a formed spring flexing pawl 164. The needle shuttle may be positioned such that it is free to translate within the needle carrier body along a linear path which is parallel to the longitudinal axis of the screw shaft. The linear path of the needle shuttle has a length defined by the slots located on the lateral sides of the carrier body. Variable adjustment of the skin piercing elements 23 may be accomplished by pressing the adjustment buttons 162, which protrude through the lateral slots 154, inward as shown in FIG. 45, which results in disengagement of the pawls 164 from the adjustment racks 152, thereby permitting translational adjustment of the needle shuttle 160 along the slot path. Releasing the adjustment buttons causes the pawl to automatically engage the adjustment rack, thus preventing slippage and affording secure repositioning of the needle shuttle within the needle carrier body.

According to the preferred embodiment, the needle carrier 150 exhibits a vacuous needle carrier body with integrally associated adjustment racks 152 positioned along opposing lateral interior surfaces of the carrier body. Additionally, parallel coplanar slots 154 are situated within both lateral surfaces of the carrier body as shown in FIG. 43. A needle shuttle 160 situated within the void defined by the carrier body exhibits a plurality of skin piercing elements 23 positioned on the anterior surface thereof; integral adjustment buttons 162, which protrude through the lateral slots 154 situated in the carrier body; and spring flexing pawls 164 integrally associated with each adjustment button. The translational adjustment of skin piercing elements 23 permits the trapping of the tissue between the skin piercing elements 23 and the needle carrier, thereby preventing rotation of the needles out of the skin when high stretching force is applied.

Figure 47:
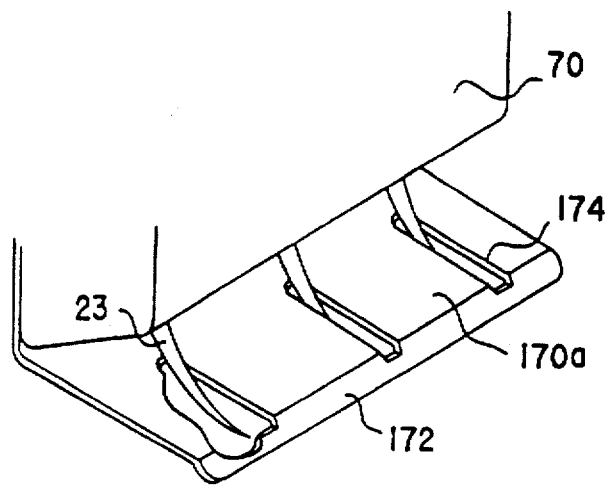
FIG. 47 shows an enlarged perspective view of a needle carrier of an alternative embodiment of the invention exhibiting a skin insertion element shield.
Figure 48:
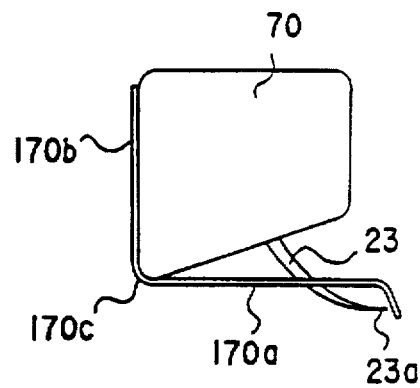
FIG. 48 shows a side view in elevation of the apparatus of FIG. 47.
Figure 49:
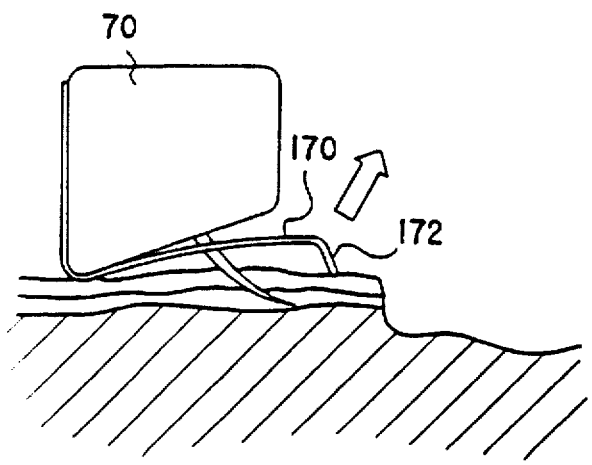
FIG. 49 shows a side view in elevation of the apparatus of FIG. 47 shown engaging a surface of the skin with the shield retracted.

FIGS. 47–49 show a further advantageous embodiment of a retaining member 70 of a skin closing apparatus, which may exhibit a plurality of skin insertion needles 23, and a device for shielding the skin insertion needles. According to this embodiment of the invention, the shield 170 may include a substantially horizontal flexible member 170a exhibiting a flange 172 extending from an anterior edge thereof at an acute angle relative to the upper surface thereof. The flexible member 170a exhibits a plurality of longitudinal slots 174 corresponding to each needle 23 protruding from the retaining member 70, each slot extending substantially perpendicular relative to the anterior edge of the shield. The needles 23 pass through the slots 174 such that the needle points 23a rest behind the shield flange 172. The posterior edge of the shield may be flexibly attached to the retaining element 70 by any known conventional means.

According to the preferred embodiment, the shield 170 exhibits a substantially L-shaped cross section comprised of horizontal flexible member 170a and a substantially vertical member 170b. The vertical member 170b and horizontal member 170a are integrally connected at a bend 170c. The vertical member 170b is fixed to the back side of the retaining element 70. Configuration of the shield and retaining elements in this fashion allows the invention to approximate tissue while protecting the user from exposed needles. To approximate the tissue the needles and the shield are pressed against the skin, which automatically deflects the shield upward, so that the needles are allowed to penetrate the tissue.

FIGS. 50–52 show a further advantageous embodiment of a retaining member 70 of a skin closing apparatus exhibiting a base segment or needle carrier 71 which may incorporate a device for shielding the exposed needles 23 of a skin closing apparatus. According to this embodiment of the invention, the shielding device may include an independent vacuous shield 176 exhibiting at least one fingergrip 177 disposed along a lateral side of the shield, and an integral spring 178 extending from an upper surface of the vacuous shield 176. Additionally, the vacuous shield may exhibit at least one pin 180 for slidably engaging a corresponding slot 181 in the body of the needle carrier 71, and at least one tab 182 for slidably engaging a track 183 formed in a surface of the needle carrier 71.

A preferred embodiment of the device includes a vacuous shield 176 having a downwardly sloping surface forming an anterior shield surface 184, which forms an acute angle relative to the upper, substantially horizontal surface of the vacuous shield. The shield exhibits two integrally associated finger grips 177 symmetrically disposed on each external lateral surface of the vacuous shield. Further, an integral spring 178 extends horizontally from the upper surface of the shield and engages the upper surface of the needle carrier so as to provide a restoring force once the shield has been displaced along a predetermined path. The vacuous shield also includes two pins 180, each positioned and centered along an opposing internal lateral side of the vacuous shield. Each pin 180 slidably engages a slot 181 formed in each lateral side of the needle carrier 71. This configuration permits the shield to be fixedly mounted to the needle holder so that the pin 180 of the shield can travel from one end of the slot to the other thereby permitting the shield to be retracted or engaged. The vacuous shield also exhibits a two integrally formed tabs 182 each formed along an opposing interior lateral surface of the vacuous shield. Each tab 182 is slidably received in a track 183 formed in a corresponding lateral surface of the needle carrier, so as to guide the vacuous shield during retraction and replacement operations.

Release of the shield lock is achieved by pushing the finger grips 177 rearward, as shown in FIG. 52, thus moving the pin 180, to the rear portion of the slot 181, and aligning the tabs 182, with the upper portion of the track 183. This position will allow the shield to pivot about the pin 180, as the tab 182, travels along the track 183. This movement exposes the skin piercing elements 23, for tissue approximation. As the shield tilts upward, to expose the needles, its integral return spring 178 is put into tension. When the device is removed from the tissue, the return spring automatically brings the shield down over the needles. Locking the shield is achieved by pulling the shield grips 177 forward.

The vacuous shield protects the user from exposed skin piercing elements by providing an automatic and lockable shield return, once the needle carrier is removed from the tissue.

Figure 53:
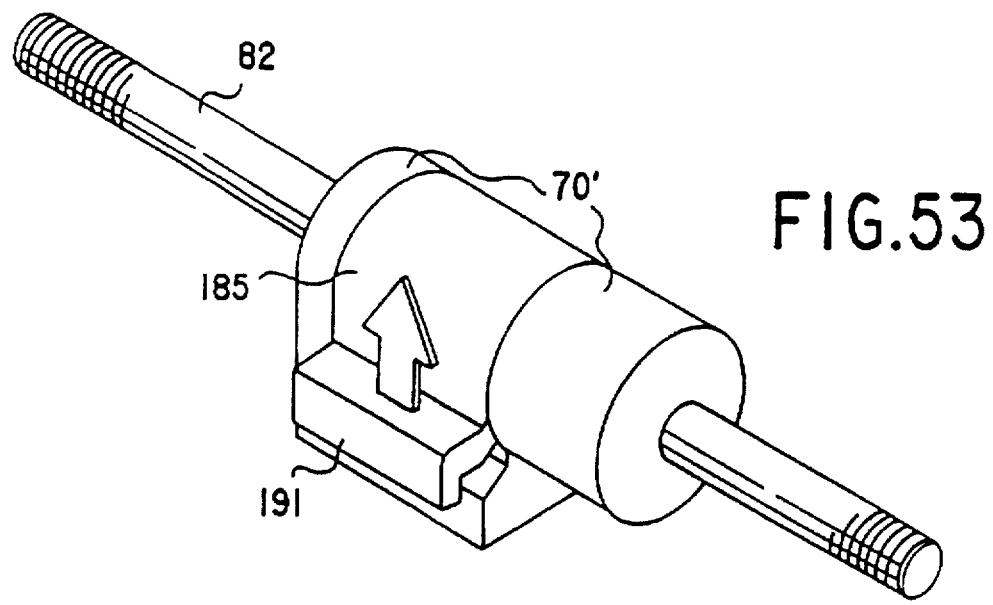
FIG. 53 shows an enlarged perspective view of a retaining member of the invention exhibiting a pivoting member according to an alternative embodiment.
Figure 54:
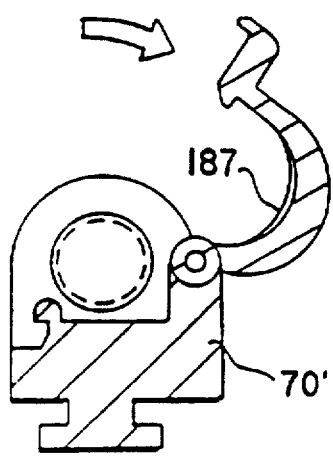
FIG. 54 shows a sectional end view of the apparatus of FIG. 53 with the locking member in an open position.
Figure 55:
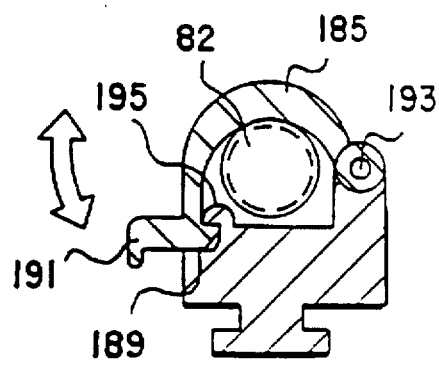
FIG. 55 shows a sectional end view of the apparatus of FIG. 53 with the locking member in a closed position.

FIGS. 53–55 show an alternate embodiment of a pivoting lock 185 designed for use with a skin closing apparatus. According to this embodiment of the invention, retaining member 70' may exhibit a lock 185 for releasably locking the retaining member 70' to the screw 82. The retaining member 70' exhibits a smooth bore which permits free movement of the retaining member 70' along the longitudinal axis of the screw 82. The pivoting lock 185 exhibits a threaded portion 187, which allows one to lock the retaining member into threaded engagement with the screw shaft 82. The lock may also be biased i.e., by the resilience of the material selected, so the lock may stay in either the closed or open position. In addition, the pivoting lock, may include a latch 189 for securing the pivoting lock in a closed position, and a release bar 191 which permits a user to release the pivoting lock from the engaged position.

According to the preferred embodiment, the pivotable lock 185 is secured and configured so as to pivotally engage the retaining member 70' by pivot pin 193 at a pivot point. The retaining member includes an integral locking tab 195 for receiving and securing an integral latch 189 of the pivoting lock 185 when the lock is in the closed position. A portion of the inner surface of the pivoting lock member 185 exhibits a contoured and threaded inner engagement surface 187 having a contour and thread gage which matches that of the threaded screw shaft 82. When the pivot locking member is in the closed position, as shown in FIG. 55, the threaded inner engagement surface 187 secure the retaining member in threaded engagement with the screw shaft 82. When the pivot lock member 185 is in the open position, as shown in FIG. 54, the retaining member 70' is released from and capable of translational movement along the threaded screw shaft 82.

The principal advantages realized as a result of this configuration are the lock's ability to provide for positive closure in addition to its ability to accurately self align while simultaneously providing for swift engagement or disengagement of the tension bar. For example, the lock may be opened swiftly and easily by lifting up on the release bar 191, which causes the pivotable lock 185, to flex slightly thus allowing the latch 189, to disengage the integral locking tab 195. Continued rotation of the pivotable lock 185 in a counter clockwise direction, as shown in FIG. 54, about the pivot 193 causes the contoured and threaded engagement surface 187 of the pivotable lock 185, to disengage the threads exhibited by tension bar 82. Alternatively, the lock may be closed, or engaged, by rotating the release bar counterclockwise, as shown in FIG. 55, until the latch 189 automatically engages the locking tab 195, which causes the inner contoured and threaded engagement surface 187 of the pivotable lock 185, to securely engage, and slightly shift the threaded tension bar 82 on its axis, thereby resulting in self alignment.

FIGS. 56 and 57 show the preferred embodiment of the long interdermal needles, which may exhibit a cross-section of three edges or five edges. Each interdermal needle 210 exhibits a straight shaft 211 with a tapered point 211a.

According to the preferred embodiment, the interdermal needle is made of surgical steel. The straight shaft may be connected to a handle 212 that includes an offset portion 213. The handle and shaft may be connected by gluing or welding. The offset handle facilitates manipulation and insertion of the long interdermal needles. A protective covering 220 may be provided. The covering may exhibit wings or extensions 221 for easy disassembly of the protective covering from the long interdermal needle.

FIGS. 58 and 59 show an embodiment of the skin stretching device configured with a protective covering 230. According to the preferred embodiment a clear plastic cover is provided so the user may see the skin piercing elements. The cover also protects the skin piercing elements during handling and shipping. Further, the cover protects the surgeon from injury.

FIG. 60 shows a retractor 240 for use with the skin closing device. Preferably, the retractor is substantially the same length of the skin stretching device and enhances placement and alignment of the device about the skin defect. The retractor should have a traumatic ends 241, 242, which may be configured with curved edges 243.

The device may also be configured with blunt needles or hooks in lieu of skin piercing elements. A sharp stylet may be used to puncture the skin. The blunt needles of the retaining members may then be inserted into the punctured areas. The blunt needle configuration provides an important safety feature as the surgeon may be cut by the skin piercing elements and infected with a patient's body fluids. The device and use of the device is otherwise identical to the above-described embodiments.

According to the preferred embodiment, the screw shaft is made of 30% glass fiber and 15% PTFE filled polycarbonate. The indicator and bushing are made of polyamide (nylon) 6/6. The skin insertion elements and long interdermal needles are made of surgical stainless steel, and all other parts are made of "Lexan" polycarbonate.

In summary, the device is contemplated for use with wide wounds or skin defects. A large wound may be caused by a gunshot, a different trauma, surgery, or a cancer and may require removal. After excising the margins of a large wound to be closed, if necessary, a surgeon would insert the two long interdermal needles in the opposing edges of the skin.

Next, the surgeon would place the two retaining members on opposite sides of the wound, while hooking the skin insertion elements on either end underneath the long interdermal needles. It should be noted that the long interdermal needles may be inserted deeper than the skin level, i.e., into the fascia. It should also be noted that the two retaining members may be disassembled prior to placement about the wound and subsequently reassembled prior to approximation. Once both ends of a retaining member are hooked the surgeon can quickly bring the ends together until a certain amount of resistance to closing the tissue is encountered.

At that time, the reversible lock may be snapped into the locked threaded position so the retaining members are connected in threaded engagement. The surgeon may begin turning the knob and applying stretching forces until reaching a recommended force, as indicated by a number on the scale of the force level indicator.

Where the skin stretching device includes topical engagement elements rather than skin piercing or skin insertion elements, the topical engagement elements may be engaged with the interdermal needles by first placing the skin closing apparatus about the wound such that retaining members are disposed about opposing margins of the wound. The interdermal needles are woven into the skin, out of the skin, through a topical engagement element extending from a first leg, into the skin, out of the skin and through a topical engagement element extending from a second leg, and into the skin again. Once all topical engagement member have engaged the respective exposed portions of the interdermal needles, the surgeon can quickly bring the retaining members together until a certain amount of resistance to closing the tissue is encountered. Next, the reversible lock may be snapped into the locked threaded position so the retaining members are connected in threaded engagement. The edges of the wound are then approximated by applying force to the contracting mechanism through a force limiting element to bring one margin of the skin defect toward another margin of the skin defect without exceeding a predetermined force.

Alternatively, where the skin engaging element is a topical engagement member, such as recess 126 or clip 125, the interdermal needles first may be woven through the skin so portions of them are visible. The skin stretching device may then be placed about the wound so that the topical engagement elements are disposed proximal to the exposed portions of the interdermal needles. The interdermal needles may then be engaged by passing the exposed portions of the interdermal needles through the openings in the respective topical engagement members. Once all topical engagement members have engaged the respective exposed portions of the interdermal needles, the surgeon can quickly bring the ends together until a certain amount of resistance to closing the tissue is encountered. Next, the reversible lock may be snapped into the locked threaded position so the retaining members are connected in threaded engagement. The surgeon may begin turning the knob and applying stretching forces until reaching a recommended force, as indicated by a number on the scale of the force level indicator.

An advantage of the invention is realized in the event that the surgeon continues to turn the knob. The force applied is at a maximum level and cannot be exceeded. The force will not increase as the clutch has disengaged. During the application of force the spring has compressed while the retaining members are being brought together. And the indicator moves along the scale, the surgeon may visualize the application of increasing force.

The inventors note that a visualization also occurs when the spline disengages, as the indicator no longer moves to a higher value. The surgeon also receives tactile feedback that there is no more force being applied. In this regard the device is self-regulating. According to the preferred embodiment, the skin stretching device has a certain constant spring rate, Hooke's constant for the spring. The visco-elastic properties of the skin allows the skin to stretch, and the compressed spring expands while returning essentially to its original, rest position.

The retaining members also come together simultaneously with the spring expansion. The indicator shows that the force level is decreasing. The indicator shows movement, i.e., so an observer can see that the device is still working. The clutch also reengages so the surgeon may perform additional skin stretching operations. These operations are repeated in intervals until the skin comes together. The spring and the force limiting action significantly control stretching operation. As the skin relaxes, the device returns essentially to its original rest position. It's very easy to visualize the stretching and relaxation of the skin. In that regard the device functions as a feedback system.

It is also contemplated for a wound of significant dimensions to use the device to close an area of skin, apply sutures to that area and reposition the device on another part of that wound or on another wound on the same patient. It is further contemplated to use multiple devices on a single patient or wound simultaneously.

The illustrated embodiments are shown by way of example. The spirit and scope of the invention is not to be restricted by the preferred embodiments shown.

What is claimed is:

1. A skin defect closing device comprising:

two skin engaging means for engaging skin along opposing margins of a skin defect;

approximating means, attached to both said skin engaging means, for approximating one said skin engaging means to a second said skin engaging means along opposing margins of said skin defect;

force limiting means, connected to said approximating means, for limiting a force applied by said means for approximating to said means for engaging; and alignment means, connected to said approximating means, for maintaining alignment of the skin closing device with the margins of the skin defect.

2. The skin defect closing device according to claim 1, wherein said force limiting means comprises a clutch connected to said approximating means and configured so a force applied along the margins of the skin defect by said approximating means is limited to a predetermined value.

3. The skin defect closing device according to claim 2, wherein said clutch exhibits:

a male engaging member exhibiting a single radially extending spline; and a female engaging member exhibiting a plurality of radial splines and defining a recess configured to receive said male member.

4. The skin defect closing device according to claim 3, wherein each of said splines exhibits an oblique contact surface.

5. The skin defect closing device according to claim 1, wherein the two skin engaging means comprises:

a plurality of interdermal needles configured for insertion into the skin along said opposing margins of the skin defect such that at least longitudinal portions of each of said interdermal needles are visible; and a plurality of needle engaging elements configured for engaging the visible portions of the interdermal needles.

6. The skin defect closing device according to claim 5, wherein said needle engaging element is a loop.

7. The skin defect closing device according to claim 5, wherein said needle engaging element is a suture.

8. The skin defect closing device according to claim 5, wherein said needle engaging element is a clip.

9. The skin defect closing device according to claim 5, wherein said needle engaging element is a terminal portion of a leg configured in the shape of an orifice or recess.

10. The skin defect closing device according to claim 1, wherein said alignment means comprises:

a plurality of retaining members, each of said retaining members exhibiting a base member and a flange having a first end connected to said base member and a second end connected to said approximating means;

a plurality of needle carriers, each of said needle carriers pivotally connected to a surface of said base member and exhibiting a plurality of skin insertion elements.

11. The skin defect closing device according to claim 1, wherein said two skin engaging means comprises:
   a first retaining member exhibiting a first base member, said first base member exhibiting:
      a plurality of skin insertion elements, each of said skin insertion elements protruding from a surface of said first base member;
      at least a male engaging member protruding from a surface of the first base member; and
   a second retaining member exhibiting a second base member, said second base member exhibiting:
      a plurality of skin insertion elements, each of said skin insertion elements protruding from a surface of said second base member;
      at least a female engaging member protruding from a surface of the second base member, said female engaging member configured to receive and retain said male engaging member once said retaining members have been fully approximated.

12. The skin defect closing device according to claim 11, wherein said first base member is detachably connected to said first retaining member, and said second base member is detachably connected to said second base member.

13. The skin defect closing device according to claim 1, wherein said two skin engaging means are detachably connected to said means for approximating.

14. The skin defect closing device according to claim 1, wherein said two skin engaging means comprises two retaining members, each retaining member exhibiting:
   a vacuous needle carrier body; and
   a needle shuttle slidably disposed within said vacuous needle carrier body, said needle shuttle exhibiting a plurality of skin insertion elements protruding from a surface of said needle shuttle.

15. The skin defect closing device according to claim 1, further comprising means for shielding a plurality of skin insertion elements attached to said two skin engaging means, said two skin engaging means each comprising a base member having a surface from which said plurality of skin insertion elements extend.

16. The skin defect closing device according to claim 15, wherein said means for shielding comprises a flexible substantially planar shield having a first end fixed to said base member and a second end exhibiting a flange extending at an acute angle with respect to an upper surface of said shield.

17. The skin defect closing device according to claim 15, wherein said means for shielding comprises a vacuous shield retractably connected to said base member and configured to cover said plurality of skin insertion needles.

18. A skin closing apparatus according to claim 1:
   wherein each of said two skin engaging means comprises a retaining member having a plurality of skin insertion elements for insertion into the skin along margins of the skin defect;
   wherein said approximating means comprises a contracting mechanism connecting said retaining member and wherein said force limiting means comprises a clutch configured so a force applied along the margins of the skin defect by said contracting mechanism is limited to a predetermined value.

19. The skin closing apparatus according to claim 18, wherein said contracting mechanism exhibits a plurality of contractor arms in substantially parallel alignment, each of said contractor arms supporting one said retaining member in a sliding arrangement.

20. The skin closing apparatus according to claim 19, wherein each of said contractor arms exhibits a straight, smooth bar at one end, each of said retaining members further exhibiting a retaining member support bore configured so said contractor arm bar passes through said retaining member support bore.

21. The skin closing apparatus according to claim 19, wherein one of said contractor arms exhibits a contractor arm smooth bore, and another of said contractor arms exhibits a contractor arm screw-threaded bore.

22. The skin closing apparatus according to claim 21, further comprising a screw connecting said contractor arms and exhibiting a screw-threaded portion engaging said contractor arm screw-threaded bore.

23. The skin closing apparatus according to claim 21, wherein each of said contractor arms exhibits a plurality of lugs, each of said lugs defining one of said contractor arm bores.

24. The skin closing apparatus according to claim 19, further comprising a cylindrical bar, wherein each of said contractor arms further exhibits an alignment bore; said cylindrical bar extending through said alignment bores.

25. The skin closing apparatus according to claim 18, wherein each of said retaining members exhibits two legs and a flange connecting said legs and defining a flange bore exhibiting an axis in substantially parallel alignment with axes of said legs.

26. The skin closing apparatus according to claim 25, wherein one of said flange bores is a threaded flange bore, another of said flange bores is a smooth flange bore, said contracting mechanism comprising at least a screw extending through said flange bores.

27. The skin closing apparatus according to claim 18, wherein said retaining member further comprise two U-shaped retaining members, each of said U-shaped retaining members exhibits two legs and a flange connecting said legs.

28. The skin closing apparatus according to claim 18, further comprising a plurality of interdermal needles for engagement by said skin insertion elements.

29. The skin closing apparatus according to claim 28, wherein said plurality of interdermal needles comprises two interdermal needles.

30. The skin closing apparatus according to claim 18, wherein said clutch is a frictional clutch.

31. The skin closing apparatus according to claim 18, wherein said clutch exhibits a male spline and a female spline defining a recess configured to receive said male spline.

32. The skin closing apparatus according to claim 18, wherein a distance between each said retaining member defines an axis, said clutch exhibits a plurality of splines, one of said splines configured as an axially stationary spline, another of said splines configured as an axially movable spline.

33. The skin closing apparatus according to claim 32, wherein each of said splines exhibits an oblique contact surface.

34. The skin closing apparatus according to claim 18, further comprising a force level indicator connected to said contracting mechanism and for indicating the force applied along the margins of the skin defect.

35. A skin defect closing apparatus comprising:
   a plurality of retaining members, each of said retaining members exhibiting:
      at least two legs,
      a flange connecting said legs and exhibiting a flange bore located between said legs,
      a plurality of needle engaging elements, each of said needle engaging elements protruding from a surface of one of said legs; and a contracting mechanism connecting said retaining members and engaging one of said flange bores, said contracting mechanism configured to approximate said retaining members.

36. The skin defect closing apparatus according to claim 35, further comprising a plurality of interdermal needles configured for insertion into the skin along opposing margins of the wound such that portions of said interdermal needle are disposed above the surface of the skin for engagement by said needle engaging elements.

37. The skin defect closing apparatus according to claim 36, wherein the plurality of interdermal needles are woven through the skin such that said interdermal needles emerge from the skin at least twice so that the needle engaging elements protruding from each leg of the retaining members may engage with the interdermal needles topically.

38. The skin defect closing apparatus according to claim 35, wherein each of said retaining members is configured so said legs are in parallel alignment.

39. The skin defect closing apparatus according to claim 35, wherein each of said needle engaging elements comprises a loop.

40. The skin defect closing apparatus according to claim 35, wherein each of said needle engaging elements comprises a suture.

41. The skin defect closing apparatus according to claim 35, wherein each of said needle engaging elements comprises a clip.

42. The skin defect closing apparatus according to claim 35, wherein each of said needle engaging elements comprises an orifice or recess disposed in the terminal portion of the leg.

43. The skin defect closing apparatus according to claim 35, wherein each of said retaining members is configured so said legs are in parallel alignment.

44. The skin defect closing apparatus according to claim 35, further comprising two interdermal needles, each of said interdermal needles is configured for insertion underneath skin proximal to a margin of a skin defect, each of said skin insertion elements engaging one of said interdermal needles.

45. The skin defect closing apparatus according to claim 35, wherein said plurality of retaining members comprises two retaining members.

46. The skin defect closing apparatus according to claim 18, wherein each of said skin insertion elements is a skin-piercing hook, said plurality of skin-piercing hooks comprising two skin-piercing hooks.

47. The skin defect closing apparatus according to claim 35, wherein said contracting mechanism comprises at least a screw.

48. The skin defect closing apparatus according to claim 47, wherein one of said flange bores is a screw-threaded flange bore, said screw engaging said screw-threaded flange bore.

49. The skin defect closing apparatus according to claim 47, wherein one of said retaining member flange bores is a smooth bore, said screw exhibits a collar configured to contact said retaining member exhibiting said smooth bore, said screw extending through said smooth bore.

50. The skin defect closing apparatus according to claim 47, wherein one of said retaining members exhibits a reversible lock having at least a locking threaded element and configured so said locking threaded element engages said screw, when said reversible lock is in a locked position.

51. The skin defect closing apparatus according to claim 35, wherein said at least two retaining members further comprise two U-shaped retaining members, each of said U-shaped retaining members exhibits two legs and a flange connecting said legs.

52. The skin defect closing apparatus according to claim 35, further comprising a plurality of interdermal needles configured so said retaining members engage said interdermal needles, when said contracting mechanism approximates said retaining members.

53. The skin defect closing apparatus according to claim 52, wherein said plurality of interdermal needles comprises two interdermal needles.

54. The skin defect closing apparatus according to claim 52, wherein each of said plurality of interdermal needles exhibits a handle and a straight interdermal needle shaft connected to said handle.

55. The skin defect closing apparatus according to claim 54, wherein said handle exhibits a portion offset from said straight interdermal needle shaft.

56. The skin defect closing apparatus according to claim 35, further comprising a force level indicator connected to said contracting mechanism and for indicating the force applied along the margins of the skin defect.

57. The skin defect closing apparatus according to claim 56, wherein said force level indicator exhibits a plurality of numerals, each of said numerals representing a different level of force applied along the margins of the skin defect.

58. The skin defect closing apparatus according to claim 35, wherein said contracting mechanism exhibits a clutch configured so a force applied along the margins of the skin defect by said contracting mechanism is limited to a predetermined clause.

59. The skin defect closing apparatus according to claim 58, wherein said clutch is a frictional clutch.

60. The skin defect closing apparatus according to claim 58, wherein said clutch exhibits a male spline and a female spline defining a recess configured to receive said male spline.

61. The skin defect closing apparatus according to claim 58, wherein a distance between said retaining members defines an axis, said clutch exhibits a plurality of splines, one of said splines configured as an axially stationary spline, another of said splines configured as an axially movable spline.

62. The skin defect closing apparatus according to claim 61, wherein each of said splines exhibits an oblique contact surface.

63. The skin defect closing apparatus according to claim 61, wherein said clutch further exhibits a biasing element configured so said axially movable spline is biased toward said axially stationary spline.

64. The skin defect closing apparatus according to claim 35, wherein each of said retaining members exhibits a pivotal base element configured so said base element rotates about a reference position on said retaining member.

65. The skin defect closing apparatus according to claim 64, wherein each of said retaining members further exhibits a stop for limiting rotational movement of said pivotal base element.

66. The skin defect closing apparatus according to claim 64, wherein said pivotal base element is further configured so said base element rotates from about 0° to about ±20° the reference position on said retaining member.

67. A skin defect closing apparatus comprising:
   a plurality of retaining members, each of said retaining members exhibiting:
      a base member,
      a flange connected to said base member and exhibiting a flange bore;

a plurality of skin insertion elements, each of said skin insertion elements protruding from a surface of said base member; and a contracting mechanism connecting said retaining members and engaging one of said flange bores, said contracting mechanism configured to approximate said retaining members.

68. The skin defect closing apparatus according to claim 67, wherein said base member further comprises:

a base plate having an upper surface connected to a lower surface of said flange; and a needle carrier pivotally connected to said base plate, said needle carrier exhibiting at least two legs, each of said skin insertion elements protruding from a surface of one of said legs.

69. The skin defect closing apparatus according to claim 68, wherein said base member further comprises a pivotal link connecting said base plate to said needle carrier.

70. The skin defect closing apparatus according to claim 69, wherein said base plate, said needle carrier and said pivotal link comprise a one-piece integral member.

71. The skin defect closing apparatus according to claim 67, wherein said plurality of retaining members comprise:

a first retaining member exhibiting a first base member, said first base member further exhibiting at least a male engaging member protruding from a surface of the first base member; and a second retaining member exhibiting a second base member, said second base member further exhibiting at least a female engaging member protruding from a surface of the second base member, said female engaging member configured to received and retain said male engaging member once said retaining members have been fully approximated.

72. The skin defect closing apparatus according to claim 71, wherein said first base member further exhibits a female engaging member protruding from a surface of said first base member; and said second base member further exhibits a male engaging member protruding from a surface of said second base member, said female engaging member of said first base member configured to receive and retain said male engaging member of said second base member once said retaining members have been fully approximated.

73. The skin defect closing apparatus according to claim 67, wherein said first base member is detachably connected to a flange of said first retaining member and said second base member is detachably connected to a flange of said second retaining member.

74. The skin defect closing apparatus according to claim 67, wherein said base member is detachably connected to said flange.

75. The skin defect closing apparatus according to claim 74, wherein said flange exhibits an engaging stud protruding from a surface of the flange, and said base member exhibits an engaging receptacle formed in a surface of the base member for detachably receiving said engaging stud.

76. The skin defect closing apparatus according to claim 67, wherein said base member comprises:

a vacuous needle carrier body; and a needle shuttle slidably disposed within said vacuous needle carrier body, said plurality of skin insertion elements protruding from a surface of said needle shuttle.

77. The skin defect closing apparatus according to claim 76, wherein said vacuous needle carrier body comprises:

at least one adjustment rack disposed along each lateral surface of said vacuous needle carrier body; and at least one slot formed in each said lateral surface of said vacuous needle carrier body.

78. The skin defect closing apparatus according to claim 77, wherein said needle shuttle comprises:

at least one spring flexing pawl, each configured to releasably engage one of said at least one adjustment rack; and at least one adjustment button, each connected to one of said at least one spring flexing pawl and extending through one of said at least one slot in said vacuous needle carrier body, said adjustment button configured to release said at least one spring flexing pawl from engagement with said at least one adjustment rack upon actuation of the adjustment button.

79. The skin defect closing apparatus according to claim 67, further comprising:

a flexible shield attached to each of said plurality of retaining members and configured to shield points of said skin insertion elements.

80. The skin defect closing apparatus according to claim 79, wherein said flexible shield includes an upper substantially planar member and a lower substantially planar member attached to and extending substantially perpendicular from said upper planar member, such that the flexible shield exhibits a substantially L-shaped cross section.

81. The skin defect closing apparatus according to claim 80, wherein said upper substantially planar member is fixed to said retaining member.

82. The skin defect closing apparatus according to claim 80, further comprising an integral flange extending from a free end of said lower substantially planar member at an acute angle with respect to an upper surface of said shield, and configured to shield the points of said skin insertion elements.

83. The skin defect closing apparatus according to claim 80, wherein said lower substantially planar member exhibits a plurality of parallel slots for receiving said skin insertion elements.

84. The skin defect closing apparatus according to claim 67, wherein said contracting mechanism comprises at least a threaded screw shaft.

85. The skin defect closing apparatus according to claim 84, wherein one of said retaining members exhibits a pivoting lock having at least a locking threaded element and configured so said locking threaded element engages said screw, when said pivoting lock is in a locked position.

86. The skin defect closing apparatus according to claim 67, further comprising a vacuous pivoting shield connected to said base member and configured to shield said skin insertion elements when in a closed position.

87. The skin defect closing apparatus according to claim 86, wherein said vacuous pivoting shield comprises:

a shield body exhibiting at least a downward sloping anterior surface connected to an upper surface, said upper surface slidably disposed on an upper surface of said base member;

an integrally formed spring extending from said upper surface of said shield body;

at least one integrally formed pin, each protruding from an interior lateral surface of said shield body and configured to slidably engage a corresponding slot in a lateral surface of said base member;

at least one integrally formed tab, each protruding from said interior lateral surface of said shield body and configured to slidably engage a corresponding slide path in said lateral surface of said base member; and at least one finger grip, each disposed on an exterior lateral surface of said shield body.

88. The skin defect closing apparatus according to claim 67, wherein said contracting mechanism exhibits a clutch configured so a force applied along the margins of the skin defect by said contracting mechanism is limited to a predetermined value.

89. The skin defect closing apparatus according to claim 88, wherein said clutch exhibits a male engaging member and a female engaging member defining a recess configured to receive said male engaging member.

90. The skin defect closing apparatus according to claim 89, wherein said male engaging member exhibits one radial extending spline, and said female engagement member exhibits a plurality of corresponding radial splines.

91. The skin defect closing apparatus according to claim 90, wherein a distance between said retaining members defines an axis, said female engaging member configured as an axially stationary engaging member, and said male engaging members configured as an axially movable engaging member.

92. The skin defect closing apparatus according to claim 91, wherein each of said engaging members exhibits an oblique contact surface.

93. The skin defect closing apparatus according to claim 91, wherein said clutch further exhibits a biasing element configured so said axially movable engaging member is biased toward said axially stationary engaging member.

94. A method of closing a wide skin defect comprising the steps of:

locating retaining members about opposing margins of the skin defect;

inserting interdermal needles into skin along said opposing margins of the skin defect and into engagement with said retaining members;

applying force to a contracting mechanism through a force limiting element to bring one margin of the skin defect toward another margin of the skin defect without exceeding a predetermined force.

95. The method of closing a wide skin defect according to claim 94, wherein the step of inserting the interdermal needle further comprises the steps of:

weaving the interdermal needle into the skin, out of the skin, through a first topical engagement element of one of said retaining members, into the skin again, out of the skin and through a second topical engagement element of one of said retaining members into the skin again.

96. The method of closing a wide skin defect according to claim 94, wherein the step of inserting the interdermal needles further comprises the steps of:

weaving the interdermal needle into the skin, out of the skin, into the skin again, out of the skin again, and into the skin again;

engaging exposed portions of the interdermal needle with a plurality of topical engagement elements extending from a surface of each of said retaining members.

97. The method of closing a wide skin defect according to claim 94, further comprising the steps of:

observing skin relaxation as indicated by decreasing values on a force level indicator; and reapplying force to a contracting mechanism so the retaining members engage the interdermal needles and bring one margin of the skin defect toward another margin of the skin defect, when a predetermined force level is indicated on the force level indicator.

98. A skin defect closing apparatus comprising:

a plurality of retaining members, each of said retaining members exhibiting:

at least two legs, a flange connecting said legs and exhibiting a flange bore located between said legs, a plurality of needle engaging elements, each of said needle engaging elements protruding from a surface of one of said legs; and a contracting mechanism connecting said retaining members and engaging one of said flange bores, said contracting mechanism configured to approximate said retaining members;

a plurality of interdermal needles configured for insertion into the skin along opposing margins of the wound such that portions of said interdermal needle are disposed above the surface of the skin for engagement by said topical engagement elements.

99. A skin closing apparatus for closing skin defects comprising:

at least two retaining members, each of said retaining members exhibiting a plurality of skin insertion elements for insertion into the skin along margins of the skin defect;

a contracting mechanism connecting said retaining members;

a plurality of interdermal needles configured for insertion into the skin along opposing margins of the wound such that portions of said interdermal needle are disposed above the surface of the skin for engagement by said needle engaging elements.

* * * * *